United States Patent
Pack-Harris

(10) Patent No.: US 6,195,612 B1
(45) Date of Patent: Feb. 27, 2001

(54) PHARMACY BENEFIT MANAGEMENT SYSTEM AND METHOD OF USING SAME

(76) Inventor: Tama L. Pack-Harris, 5405 Renaissance Ave., San Diego, CA (US) 92122

( * ) Notice: Subject to any disclaimer, the term of this patent is extended or adjusted under 35 U.S.C. 154(b) by 0 days.

(21) Appl. No.: 09/003,082

(22) Filed: Jan. 5, 1998

(51) Int. Cl.[7] .................................................. G06F 17/60
(52) U.S. Cl. ................................................................ 702/2
(58) Field of Search .............................................. 702/2, 3

(56) References Cited

U.S. PATENT DOCUMENTS

| | | | |
|---|---|---|---|
| 5,544,044 | * 8/1996 | Leatherman | 705/3 |
| 5,845,255 | * 12/1998 | Mayaud | 705/3 |
| 5,918,208 | * 6/1999 | Javitt | 705/2 |

OTHER PUBLICATIONS

Jones, John D. "Easier to Swallow: Strategies for Managing Pharmaceutical Costs" Risk Management v43 n2 p 42(5), Feb. 1996.*

Mandelker, Jeannie "Get the Most Out of Your PBM" Business and Health v 12 n 11 p37(6), Nov. 1994.*

"For Sale: Prescribing Information" Managed Care Marketing, v2 n4, p29, no author listed, Oct. 1996.*

Banahan et al., "Using Pharmacy Computer Systems for Better Patient Care", Drug Topics, v138, n1 p80(9), Jan. 10, 1994.*

* cited by examiner

*Primary Examiner*—Melanie A. Kemper
(74) *Attorney, Agent, or Firm*—Higgs Fletcher & Mack LLP; Bernard L. Kleinke

(57) ABSTRACT

The pharmacy benefit management system includes a pharmacy computer for generating pharmacy claim information based on pharmacy activity of a medical group. A health plan computer is responsive to the pharmacy claim information for generating pharmacy activity information for the medical group. A medical group computer receives the pharmacy activity information from the health plan computer and stores the pharmacy activity information. The pharmacy activity information is processed to generate utilization information to enable the medical group to monitor the pharmacy activity.

17 Claims, 40 Drawing Sheets

▲ 1ST & 2ND QTR LIPOTROPIC UTILIZATION  PHARMATRAK
*Organization*
～702

| 710 | TOTAL COSTS | TOTAL RXS | 712<br>#RX'S<br>(30 DAYS) | 713<br>% OF RXS | 714<br>DRUG COST | % OF<br>DRUG | % OF<br>TOTAL<br>COSTS | METRIC<br>QTY | AVG COST<br>PER PRESC |
|---|---|---|---|---|---|---|---|---|---|
| LIPOTROPICS | | | 21 | 100.0% | $1,007 | 100.0% | 100.0% | | $47.95 |
| LESCOL | | | 7 | 33.3% | $238 | 23.7% | 23.7% | 210 | $34.16 |
| LESCOL 20MG CAP | | | 1 | 4.8% | $31 | 3.1% | 3.1% | 30 | $31.42 |
| LESCOL 40MG CAP | | | 5 | 23.6% | $173 | 17.1% | 17.1% | 150 | $34.51 |
| LIPITOR | | | 8 | 38.1% | $364 | 36.1% | 36.1% | 240 | $45.49 |
| LIPITOR 10MG TAB | | | 7 | 33.3% | $309 | 30.7% | 30.7% | 210 | $44.17 |
| PRAVACHOL | | | 6 | 28.6% | $404 | 40.2% | 40.2% | 180 | $67.40 |
| PRAVACHOL 20MG TAB | | | 3 | 14.3% | $160 | 15.9% | 15.9% | 90 | $53.48 |
| PRAVACHOL 40MG TAB | | | 3 | 14.3% | $244 | 24.2% | 24.2% | 90 | $81.35 |

FIG. 17 700

PRINTED 2/13/2000

*Organization* TOP 8 CLASS SUMMARY

802

LETTERMAN, DAVID  ABC MEDICAL GROUP RANCHO BERNARDO

| 810 | | | 812 # RX'S (30 DAYS) | 813 % OF RXS | 814 DRUG COST | % OF DRUG |
|---|---|---|---|---|---|---|
| | TOTAL COSTS | TOTAL RXS | | | | |
| LETTERMAN, DAVID | $2,617 | 267 | 28% | | $7,417 | |
| ACE INHIBITORS | | | 8 | 3.2% | $199 | 2.6% |
| LOTENSIN | | | 8 | 100.0% | $199 | 100.0% |
| LOTENSIN 10MG | | | 1 | 12.5% | $23 | 11.4% |
| LOTENSIN 10MG TAB | | | 2 | 25.0% | $39 | 19.4% |
| LOTENSIN 20MG TAB | | | 2 | 25.0% | $77 | 38.8% |
| LOTENSIN 5MG | | | 1 | 12.5% | $22 | 10.9% |
| LOTENSIN 5MG TAB | | | 1 | 12.5% | $19 | 9.7% |
| ALLERGY | | | 16 | 6.4% | $567 | 7.9% |
| ALLEGRA | | | 1 | 6.3% | $45 | 8.0% |
| ALLEGRA 60MG CAP | | | 1 | 6.3% | $45 | 8.0% |
| BECONASE | | | 3 | 18.8% | $101 | 17.8% |
| BECONASE AQ 0.0 | | | 3 | 18.8% | $101 | 17.8% |
| CLARITIN | | | 2 | 12.5% | $91 | 16.0% |
| CLARITIN 10MG TAB | | | 2 | 12.5% | $91 | 16.0% |
| RHINOCORT | | | 6 | 37.5% | $174 | 30.7% |
| RHINOCORT 32MCG | | | 1 | 6.3% | $33 | 5.8% |
| RHINOCORT 32MCG AER | | | 4 | 25.0% | $113 | 19.9% |
| RHINOCORT NASAL INH | | | 1 | 6.3% | $28 | 5.0% |
| VANCENASE | | | 4 | 25.0% | $156 | 27.6% |
| VANCENASE AQ .08 | | | 3 | 18.8% | $110 | 19.4% |
| VANCENASE AQ 84M | | | 1 | 6.3% | $46 | 8.1% |
| ANTIBIOTICS | | | 87 | 34.7% | $2,160 | 30.0% |
| AMOXICILLIN | | | 6 | 6.9% | $30 | 1.4% |
| AMOXICILLIN 250MG CAP | | | 1 | 1.1% | $3 | 0.1% |
| AMOXICILLIN 250MG CHW | | | 1 | 1.1% | $4 | 0.2% |
| AMOXICILLIN 250MG TAB | | | 4 | 4.6% | $23 | 1.1% |
| AMOXIL | | | 3 | 3.4% | $19 | 0.9% |
| AMOXIL 125 5ML | | | 1 | 1.1% | $3 | 0.1% |
| AMOXIL 250 5ML | | | 2 | 2.3% | $16 | 0.7% |
| AMPICILLIN | | | 1 | 1.1% | $3 | 0.1% |
| AMPICILLIN 500MG CAP | | | 1 | 1.1% | $3 | 0.1% |

FIG. 18  800

TOP 8 QUARTERLY UTILIZATION

*Organization*

PHARMATRAK

1002

LETTERMAN, DAVID  ABC MEDICAL GROUP RANCHO BERNARDO

| 1010 | 1ST QUARTER 1012 | | | 2ND QUARTER 1014 | | | 3RD QUARTER 1016 | | | FOURTH QUARTER 1018 | | |
|---|---|---|---|---|---|---|---|---|---|---|---|---|
| | % OF RX'S | DRUG COST | % OF COSTS | % OF RX'S | DRUG COST | % OF COSTS | % OF RX'S | DRUG COST | % OF COSTS | % OF RX'S | DRUG COST | % OF COSTS |
| LETTERMAN, DAVID | | 9,195.45 | | | 1,925.32 | | | | | | | |
| ACE INHIBITORS | 5.0% | 141.18 | 2.5% | 5.7% | 58.04 | 3.0% | | | | | | |
| LOTENSIN | 100.0% | 141.18 | 100.0% | 100.0% | 58.04 | 100.0% | | | | | | |
| LOTENSIN 10MG | 25.0% | 22.76 | 16.1% | | | | | | | | | |
| LOTENSIN 10MG TAB | | | | 66.7% | 38.7 | 66.7% | | | | | | |
| LOTENSIN 20MG TAB | 25.0% | 77.37 | 54.8% | | | | | | | | | |
| LOTENSIN 5MG | 25.0% | 21.67 | 15.4% | | | | | | | | | |
| LOTENSIN 5MG TAB | | | | 33.3% | 19.34 | 33.3% | | | | | | |
| ALLERGY | 6.3% | 411.1 | 7.3% | 7.9% | 155.79 | 8.1% | | | | | | |
| ALLEGRA | 10.0% | 45.14 | 11.0% | | | | | | | | | |
| ALLEGRA 60MG CAP | 10.0% | 45.14 | 11.0% | | | | | | | | | |
| BECONASE | 20.0% | 65.08 | 15.8% | 25.0% | 35.76 | 23.0% | | | | | | |
| BECONASE AQ 0.6 | 20.0% | 65.08 | 15.8% | 25.0% | 35.76 | 23.0% | | | | | | |
| CLARITIN | | | | 50.0% | 90.75 | 58.3% | | | | | | |
| CLARITIN 10MG TAB | | | | 50.0% | 90.75 | 58.3% | | | | | | |
| RHINOCORT | 50.0% | 144.7 | 35.2% | 25.0% | 29.28 | 18.8% | | | | | | |
| RHINOCORT 32MCG | 10.0% | 32.81 | 8.0% | | | | | | | | | |
| RHINOCORT 32MCG AER | 30.0% | 83.67 | 20.4% | 25.0% | 29.28 | 18.8% | | | | | | |
| RHINOCORT NASAL INH | 10.0% | 28.22 | 6.9% | | | | | | | | | |
| VANCENASE | 20.0% | 156.2 | 38.0% | | | | | | | | | |

PRINTED 2/13/2000

PMPM REPORT — 1102
PHYSICIAN LEVEL

PHARMATRAK

| 1110 | 1112 JANUARY 98 | 1114 FEBRUARY 98 | 1116 MARCH 98 | 1118 APRIL 98 | 1120 MAY 98 | 1122 JUNE 98 |
|---|---|---|---|---|---|---|
| LETTERMAN, DAVID | 9.23 | | | | | |
| HEALTH NET | 3.05 | | | | | |
| PACIFICARE | 6.18 | | | | | |

PRINTED 2/13/2000

PHYSICIAN TOP 25 DRUGS　　　　　　　　　　　　　　　　　　　　　　　　　　　PHARMATRAK
BY COSTS OR RXS

LETTERMAN, DAVID   ABC MEDICAL GROUP   RANCHO BERNARDO

| | | | DRUG COSTS | AVG COST PER PRESC | #RXS (30 DAYS) |
|---|---|---|---|---|---|
| 1 | AUGMENTIN | B | $726 | $66.01 | 11 |
| 2 | PRILOSEC | B | $684 | $85.44 | 8 |
| 3 | PREMARIN | B | $525 | $15.43 | 34 |
| 4 | PRAVACHOL | B | $404 | $67.40 | 6 |
| 5 | ZITHROMAX | B | $386 | $35.09 | 11 |
| 6 | LIPITOR | B | $364 | $45.49 | 8 |
| 7 | CEFZIL | B | $363 | $40.31 | 9 |
| 8 | PROZAC | B | $349 | $87.24 | 4 |
| 9 | SEREVENT | B | $277 | $46.18 | 6 |
| 10 | LESCOL | B | $239 | $34.10 | 7 |
| 11 | CEFTIN | B | $233 | $116.73 | 2 |
| 12 | PEPCID | B | $206 | $102.82 | 2 |
| 13 | LOTENSIN | B | $199 | $24.90 | 8 |
| 14 | RANITIDINE | G | $190 | $47.59 | 4 |
| 15 | RHINOCORT | B | $174 | $29.00 | 6 |
| 16 | ZOLOFT | B | $170 | $84.84 | 2 |
| 17 | VANCENASE | B | $156 | $39.05 | 4 |
| 18 | NAPROXEN | G | $145 | $12.08 | 12 |
| 19 | PLENDIL | B | $135 | $45.10 | 3 |
| 20 | CIPRO | B | $132 | $32.89 | 4 |
| 21 | AZMACORT | B | $122 | $40.75 | 3 |
| 22 | ALBUTEROL | G | $113 | $10.28 | 11 |
| 23 | PAXIL | B | $113 | $56.31 | 2 |
| 24 | ESTRADERM | B | $110 | $18.40 | 6 |
| 25 | DICLOFENAC | G | $107 | $17.79 | 6 |

FIG. 21

PHARMATRAK
PMPQ REPORT —— 1142
PHYSICIAN LEVEL
| 1144 | 1145 1ST QUARTER | 1146 2ND QUARTER | 1147 3RD QUARTER | 1148 4TH QUARTER |
|---|---|---|---|---|
| LETTERMAN, DAVID | 15.57 | | | |
| HEALTH NET | 3.26 | | | |
| PACIFICARE | 12.31 | | | |
FIG. 22 ↘1140    PRINTED 2/13/2000

PHYSICIAN BRANDS VS. GENERICS  PHARMATRAK

*Organization*

|  | RXS | | | BRAND | | GENERIC | |
| --- | --- | --- | --- | --- | --- | --- | --- |
|  | TOTAL | BRAND | GEN | DRUG COST | % BRAND | DRUG COST | % GENERIC |
| LETTERMAN, DAVID | 276 | 185 | 91 | $7,139 | 67.0% | $870 | 33.0% |
| COMMERCIAL | 156 | 101 | 55 | $3,796 | 64.7% | $436 | 35.3% |
| SENIOR | 120 | 84 | 36 | $3,343 | 70.0% | $433 | 30.0% |

FIG. 23

PRINTED 2/13/2000

| MAIN MENU | FIND | VIEW AS A LIST | PRESCRIPTION TABLE |

1202

ENTER THE RANGE OF DATES FOR YOUR SEARCH AS :
1/1/97...3/31/97 FOR EXAMPLE.  THEN ALSO ENTER ANY
OTHER SEARCH CRITERIA. THE MORE INFORMATION YOU
ENTER, THE SMALLER THE SAMPLE.

PHARMATRAK
THE PHARMACY BENEFIT MANAGEMENT SOFTWARE

1204

| | | | |
|---|---|---|---|
| DATE FILLED | 1/10/1998 | PAID DATE | QUARTER 1ST QUARTER 1998 |
| PHYSICIAN DEA# | AK7997402 | ID | DRUG COST 21.41 |
| THERAPEUTIC CLASS | BETA AGONIST | | DRUG ALBUTEROL 90MCG |
| PLAN | PRUDENTIAL | | PATIENT GILBERT COX |
| NETWORK | NETWORK | | DAYS SUPPLY 15 |
| MEDICAL GROUP | ABC MEDICAL GROUP | | AGE 58    SEX M |
| CLINIC | RANCHO BERNARDO | | NEW/REFILL |
| SITE/LOCATION | | | METRIC QTY 17 |
| SPECIALTY | SPECIAL DISEASES | | TOP CLASSES ☐YES ☒NO |
| SENIOR/ COMMERCIAL | COMMERCIAL | | TAGGED PHYSICIANS ONLY? |
| DISEASE STATE | | | ○YES ●NO |
| BRAND/GENERIC | G | | |

DRUG
PAXIL 20MG
PAXIL 20MG
PAXIL 20MG
PAXIL 20MG
PAXIL 20MG

THERAPEUTIC CLASS
ANTIDEPRESSANTS /
ANTIDEPRESSANTS /
ANTIDEPRESSANTS /
ANTIDEPRESSANTS /
ANTIDEPRESSANTS /

| MAIN MENU | FIND | VIEW AS A LIST | PRESCRIPTION TABLE |

1402

ENTER THE RANGE OF DATES FOR YOUR SEARCH AS :
1/1/97...3/31/97 FOR EXAMPLE. THEN ALSO ENTER ANY
OTHER SEARCH CRITERIA. THE MORE INFORMATION YOU
ENTER, THE SMALLER THE SAMPLE.

PHARMATRAK
THE PHARMACY BENEFIT MANAGEMENT SOFTWARE

1404

DATE FILLED        PAID DATE        QUARTER
PHYSICIAN DEA#     ID               DRUG COST
THERAPEUTIC CLASS                   DRUG
PLAN  HEALTH NET                    PATIENT
NETWORK                             DAYS SUPPLY
MEDICAL GROUP                       AGE 0      SEX
CLINIC                              NEW/REFILL
SITE/LOCATION                       METRIC QTY
SPECIALTY                           TOP CLASSES ☐YES ☐NO
SENIOR/ COMMERCIAL  COMMERCIAL      TAGGED PHYSICIANS ONLY?
DISEASE STATE                       ☐YES ☐NO
BRAND/GENERIC

DRUG                THERAPEUTIC CLASS

MEDICAL GROUP
TOP 8 CLASS SUMMARY

PharmaTrak

| | TOTAL COSTS | TOTAL RXS | # RX'S (30 DAYS) | % OF RXS | DRUG COST | % OF DRUG | % OF TOTAL COSTS | METRIC QTY | AVG COST PER PRESC |
|---|---|---|---|---|---|---|---|---|---|
| ACE INHIBITORS | | | 449 | 7 | $9,999 | ? | 32.8% | | $22.22 |
| ACCUPRIL | | | 32 | 4.9% | $647 | 6.5% | 2.2% | 780 | $29.41 |
| ACCUPRIL 10MG | | | 2 | 0.4% | $57 | 0.6% | 0.2% | 60 | $28.50 |
| ACCUPRIL 10MG TAB | | | 5 | 1.1% | $141 | 1.4% | 0.5% | 150 | $28.21 |
| ACCUPRIL 20MG | | | 1 | 0.2% | $57 | 0.6% | 0.2% | 60 | $56.99 |
| ACCUPRIL 20MG TAB | | | 9 | 2.0% | $238 | 2.4% | 0.8% | 300 | $26.44 |
| ACCUPRIL 5MG TAB | | | 3 | 0.7% | $68 | 0.7% | 0.2% | 90 | $22.80 |
| ALTACE | | | 4 | 0.9% | $84 | 0.8% | 0.3% | 120 | $21.12 |
| ALTACE 5MG CAP | | | 4 | 0.9% | $84 | 0.8% | 0.3% | 120 | $21.12 |
| CAPTOPRIL | | | 14 | 3.1% | $88 | 0.9% | 0.3% | 620 | $6.07 |
| CAPTOPRIL 25MG TAB | | | 11 | 2.4% | $35 | 0.4% | 0.1% | 740 | $3.22 |
| CAPTOPRIL 50MG TAB | | | 1 | 0.2% | $4 | 0.0% | 0.0% | 60 | $4.16 |
| LOTENSIN | | | 278 | 61.9% | $5,843 | 58.8% | 19.7% | 9,115 | $21.02 |
| LOTENSIN 10MG | | | 4 | 0.9% | $88 | 0.9% | 0.3% | 120 | $21.95 |
| LOTENSIN 10MG TAB | | | 109 | 24.3% | $2,271 | 22.8% | 7.7% | 3,373 | $20.84 |
| LOTENSIN 20MG | | | 5 | 1.1% | $131 | 1.3% | 0.4% | 150 | $26.22 |
| LOTENSIN 20MG TAB | | | 58 | 12.9% | $1,268 | 12.7% | 4.3% | 1,980 | $21.86 |
| LOTENSIN 40MG TAB | | | 6 | 1.3% | $99 | 1.0% | 0.3% | 157 | $16.57 |
| LOTENSIN 5MG | | | 1 | 0.2% | $22 | 0.2% | 0.1% | 30 | $21.67 |
| LOTENSIN 5MG TAB | | | 31 | 6.9% | $599 | 6.0% | 2.0% | 960 | $19.31 |
| LOTENSIN HCT 10 | | | 10 | 2.2% | $161 | 1.6% | 0.5% | 285 | $16.10 |
| LOTENSIN HCT 20 | | | 4 | 0.9% | $74 | 0.7% | 0.2% | 120 | $18.49 |
| PRINIVIL | | | 3 | 0.7% | $175 | 1.8% | 0.6% | 210 | $58.42 |

FIG. 27

Organization — MEDICAL GROUP LIPOTROPIC REPORT — PharmaTRAK™

1602

| 1610 | TOTAL COSTS | TOTAL RXS | 1612 # RX'S (30 DAYS) | 1613 % OF RXS | 1614 DRUG COST | % OF DRUG | % OF TOTAL COSTS | METRIC QTY | AVG COST PER PRESC |
|---|---|---|---|---|---|---|---|---|---|
| LIPOTROPICS | | | 492 | ? | $29,680 | ? | 100.0% | | $60.70 |
| LESCOL | | | 122 | 24.9% | $4,210 | 14.2% | 14.2% | 3,786 | $34.51 |
|   LESCOL 20MG CAP | | | 38 | 7.8% | $1,215 | 4.1% | 4.1% | 1,170 | $32.06 |
|   LESCOL 40MG CAP | | | 68 | 13.9% | $2,464 | 8.3% | 8.3% | 2,160 | $36.24 |
| LIPITOR | | | 47 | 9.6% | $2,470 | 8.3% | 8.3% | 1,480 | $52.55 |
|   LIPITOR 10MG TAB | | | 31 | 6.3% | $1,508 | 5.1% | 5.1% | 1,020 | $48.63 |
|   LIPITOR 20MG TAB | | | 6 | 1.2% | $419 | 1.4% | 1.4% | 180 | $69.80 |
|   LIPITOR 40MG TAB | | | 1 | 0.2% | $87 | 0.3% | 0.3% | 30 | $86.60 |
| PRAVACHOL | | | 258 | 52.1% | $17,746 | 59.8% | 59.8% | 8,188 | $69.59 |
|   PRAVACHOL 10MG TAB | | | 3 | 0.6% | $414 | 1.4% | 1.4% | 270 | $137.89 |
|   PRAVACHOL 20MG TAB | | | 120 | 24.5% | $6,699 | 22.6% | 22.6% | 3,843 | $55.82 |
|   PRAVACHOL 40MG TAB | | | 87 | 17.8% | $7,733 | 26.1% | 26.1% | 2,676 | $88.88 |
| ZOCOR | | | 65 | 13.3% | $5,254 | 17.7% | 17.7% | 2,115 | $80.83 |
|   ZOCOR 10MG TAB | | | 20 | 4.1% | $1,172 | 4.0% | 4.0% | 680 | $58.62 |
|   ZOCOR 20MG TAB | | | 6 | 1.2% | $569 | 1.9% | 1.9% | 180 | $94.91 |
|   ZOCOR 40MG TAB | | | 7 | 1.4% | $654 | 2.2% | 2.2% | 210 | $93.40 |
|   ZOCOR 5MG TAB | | | 3 | 0.6% | $139 | 0.5% | 0.5% | 90 | $46.48 |

FIG. 28  1600

Organization  MEDICAL GROUP
TOP 8 CLASS QUARTERLY REPORT

PHARMATRAK

1702

| 1710 | 1ST QUARTER 1712 | | | 2ND QUARTER 1714 | | | 3RD QUARTER 1716 | | | FOURTH QUARTER 1718 | | |
|---|---|---|---|---|---|---|---|---|---|---|---|---|
| | % OF RX'S | DRUG COST | % OF COSTS | % OF RX'S | DRUG COST | % OF COSTS | % OF RX'S | DRUG COST | % OF COSTS | % OF RX'S | DRUG COST | % OF COSTS |
| ACE INHIBITORS | ? | 5,992.47 | ? | ? | 3,892.85 | ? | | | | | | |
| ACCUPRIL | 6.0% | 467.39 | 7.5% | 3.9% | 189.52 | 4.9% | | | | | | |
| ACCUPRIL 10MG | 1.1% | 57 | 0.9% | | | | | | | | | |
| ACCUPRIL 10MG TAB | 1.6% | 141.06 | 2.3% | | | | | | | | | |
| ACCUPRIL 20MG | 0.5% | 56.99 | 0.9% | | | | | | | | | |
| ACCUPRIL 20MG TAB | 1.6% | 116.85 | 1.9% | 3.1% | 121.13 | 3.1% | | | | | | |
| ACCUPRIL 5MG TAB | | | | 0.8% | 68.39 | 1.8% | | | | | | |
| ALTACE | | | | 1.6% | 84.47 | 2.2% | | | | | | |
| ALTACE 5MG CAP | | | | 1.6% | 84.47 | 2.2% | | | | | | |
| CAPTOPRIL | 2.7% | 69.3 | 1.1% | 2.3% | 15.61 | 0.4% | | | | | | |
| CAPTOPRIL 25MG TAB | 1.6% | 24.01 | 0.4% | 1.6% | 11.45 | 0.3% | | | | | | |
| CAPTOPRIL 50MG TAB | | | | 0.8% | 4.16 | 0.1% | | | | | | |
| LOTENSIN | 85.8% | 3,872.64 | 88.4% | 61.7% | 2,171.16 | 55.9% | | | | | | |
| LOTENSIN 10MG | 1.1% | 87.78 | 1.4% | | | | | | | | | |
| LOTENSIN 10MG TAB | 19.8% | 1,184.48 | 19.5% | 31.3% | 1,086.71 | 28.0% | | | | | | |
| LOTENSIN 20MG | 2.7% | 131.11 | 2.2% | | | | | | | | | |
| LOTENSIN 20MG TAB | 13.2% | 796.77 | 13.1% | 14.8% | 470.12 | 12.1% | | | | | | |
| LOTENSIN 40MG TAB | | | | 3.1% | 99.44 | 2.6% | | | | | | |
| LOTENSIN 5MG | 0.5% | 21.67 | 0.4% | | | | | | | | | |
| LOTENSIN 5MG TAB | 4.4% | 278.91 | 4.6% | 7.8% | 318.6 | 8.2% | | | | | | |
| LOTENSIN HCT 10 | 1.1% | 38.7 | 0.6% | 3.1% | 122.32 | 3.1% | | | | | | |

1700  FIG. 29

PHARMATRAK

*Organization* PMPM REPORT — 1802
MEDICAL GROUP

| 1810 | 1812 JANUARY 98 | 1814 FEBRUARY 98 | 1816 MARCH 98 | 1818 APRIL 98 | 1820 MAY 98 | 1822 JUNE 98 |
|---|---|---|---|---|---|---|
| ALLBRIGHT, MADELINE | | | | | | |
| HEALTH NET | | | | | | |
| CONNICK, JR., HARRY | 1.72 | | | | | |
| HEALTH NET | 0.84 | | | | | |
| PACIFICARE | 0.88 | | | | | |
| LENO, JAY | 2.94 | | | | | |
| HEALTH NET | 1.61 | | | | | |
| PACIFICARE | 1.33 | | | | | |
| LETTERMAN, DAVID | 9.23 | | | | | |
| HEALTH NET | 3.05 | | | | | |
| PACIFICARE | 6.18 | | | | | |
| TRAVOLTA, JOHN | 7.09 | | | | | |
| HEALTH NET | 5.45 | | | | | |
| PACIFICARE | 1.64 | | | | | |

PHARMATRAK
*Organisation*
PMPQ REPORT ——— 1832
MEDICAL GROUP PACIFICARE/HEALTHNET UTILIZATION DATA
| 1834 | 1835<br>1ST QUARTER | 1836<br>2ND QUARTER | 1837<br>3RD QUARTER | 1838<br>4TH QUARTER |
|---|---|---|---|---|
| ALLBRIGHT, MADELINE | 0 | | | |
| HEALTH NET | 0.00 | | | |
| CONNICK, JR., HARRY | 9.51 | | | |
| HEALTH NET | 4.05 | | | |
| PACIFICARE | 5.46 | | | |
| LENO, JAY | 8.14 | | | |
| HEALTH NET | 3.64 | | | |
| PACIFICARE | 4.50 | | | |
| LETTERMAN, DAVID | 15.57 | | | |
| HEALTH NET | 3.26 | | | |
| PACIFICARE | 12.31 | | | |
| TRAVOLTA, JOHN | 12.89 | | | |
| HEALTH NET | 7.20 | | | |
| PACIFICARE | 5.69 | | | |
FIG. 31 ~1830

Organization — MEDICAL GROUP BRANDS VS. GENERICS — PHARMATRAK

| 1844 | 1845 TOTAL | 1847 RXS BRAND | GEN | 1846 BRAND DRUG COST | % BRAND | 1848 GENERIC DRUG COST | % GENERIC |
|---|---|---|---|---|---|---|---|
| BLACK, CLINT | 107 | 94 | 13 | $2,559 | 87.9% | $130 | 12.1% |
| COMMERCIAL | 68 | 58 | 10 | $2,200 | 85.3% | $100 | 14.7% |
| SENIOR | 39 | 36 | 3 | $1,659 | 92.3% | $30 | 7.7% |
| BOGART, HUMPHREY | 5 | | 5 | | 0.0% | $19 | 100.0% |
| COMMERCIAL | 2 | | 2 | | 0.0% | $11 | 100.0% |
| SENIOR | 3 | | 3 | | 0.0% | $8 | 100.0% |
| BOND, JAMES | 54 | 9 | 45 | $321 | 16.7% | $281 | 83.3% |
| COMMERCIAL | 54 | 9 | 45 | $321 | 16.7% | $281 | 83.3% |
| CLINTON, HILARY | 116 | 96 | 20 | $3,111 | 82.8% | $391 | 17.2% |
| COMMERCIAL | 56 | 48 | 8 | $1,564 | 85.7% | $161 | 14.3% |
| SENIOR | 60 | 48 | 12 | $1,547 | 80.0% | $230 | 20.0% |
| CONNICK, JR., HARRY | 244 | 181 | 63 | $5,148 | 74.2% | $1,251 | 25.8% |
| COMMERCIAL | 37 | 28 | 9 | $876 | 75.7% | $130 | 24.3% |
| SENIOR | 207 | 153 | 54 | $4,272 | 73.9% | $1,120 | 26.1% |
| CONNORS, DENNIS | 91 | 63 | 28 | $2,502 | 69.2% | $318 | 30.8% |
| COMMERCIAL | 32 | 20 | 12 | $908 | 62.5% | $116 | 37.5% |
| SENIOR | 59 | 43 | 16 | $1,594 | 72.9% | $202 | 27.1% |
| FORD, HARRISON | 161 | 114 | 47 | $6,160 | 70.8% | $251 | 29.2% |
| COMMERCIAL | 75 | 47 | 28 | $2,835 | 62.7% | $160 | 37.3% |
| SENIOR | 86 | 67 | 19 | $3,325 | 77.9% | $92 | 22.1% |
| GABLE, CLARK | 210 | 169 | 41 | $6,476 | 80.5% | $618 | 19.5% |
| COMMERCIAL | 115 | 91 | 24 | $3,953 | 79.1% | $246 | 20.9% |
| SENIOR | 95 | 78 | 17 | $2,523 | 82.1% | $372 | 17.9% |
| GATES, BILL | 1 | | 1 | | 0.0% | $3 | 100.0% |
| COMMERCIAL | 1 | | 1 | | 0.0% | $3 | 100.0% |
| HEPBURN, KATHERINE | 74 | 59 | 15 | $2,356 | 79.7% | $333 | 20.3% |
| COMMERCIAL | 56 | 44 | 12 | $1,722 | 78.5% | $299 | 21.5% |
| SENIOR | 18 | 15 | 3 | $634 | 83.3% | $34 | 16.7% |
| HINGIS, MARTINA | 312 | 253 | 59 | $12,100 | 81.1% | $1,196 | 18.9% |
| COMMERCIAL | 149 | 111 | 38 | $5,644 | 74.5% | $879 | 25.5% |
| SENIOR | 163 | 142 | 21 | $6,456 | 87.1% | $317 | 12.9% |

FIG. 32

Organization MEDICAL GROUP TOP 25 DRUGS BY COSTS OR RXS　　　　　　　　　　　PHARMATRAK

| 1854 | | # RX'S | DRUG COST | AVG COST PER PRESC |
|---|---|---|---|---|
| PRAVACHOL | B | 255 | $17,746 | $69.59 |
| PRILOSEC | B | 93 | $10,041 | $107.96 |
| LOTENSIN | B | 278 | $5,843 | $21.02 |
| PREMARIN | B | 418 | $5,498 | $13.15 |
| ZOCOR | B | 65 | $5,254 | $80.83 |
| PAXIL | B | 76 | $5,070 | $66.72 |
| LESCOL | B | 122 | $4,210 | $34.51 |
| PROZAC | B | 42 | $3,644 | $86.77 |
| ZOLOFT | B | 56 | $3,358 | $59.96 |
| CLARITIN | B | 50 | $2,695 | $53.91 |
| LIPITOR | B | 47 | $2,470 | $52.55 |
| RANITIDINE | G | 68 | $2,461 | $36.19 |
| ZESTRIL | B | 100 | $2,372 | $23.72 |
| TIAZAC | B | 72 | $2,356 | $32.72 |
| ZITHROMAX | B | 72 | $2,337 | $32.45 |
| DICLOFENAC | G | 57 | $2,082 | $36.52 |
| AUGMENTIN | B | 32 | $2,010 | $62.83 |
| CIMETIDINE | B | 87 | $1,986 | $22.83 |
| VANCENASE | B | 53 | $1,980 | $37.36 |
| ADALAT | B | 64 | $1,916 | $29.94 |
| ALBUTEROL | G | 101 | $1,667 | $16.50 |
| PREVACID | B | 16 | $1,604 | $100.23 |
| AEROBID | B | 11 | $1,232 | $111.96 |
| AZMACORT | B | 28 | $1,197 | $42.76 |
| ALLEGRA | B | 28 | $1,153 | $41.18 |

PHYSICIAN LIST AS OF 2/13/00

| SPECIALTY | DEA NAME | DEA ADDRESS | TELE# / FAX# |
|---|---|---|---|
| FAMILY PRACTICE | MADELINE ALLBRIGHT | 17190 BERNARDO CENTER DR. SAN DIEGO, | 619-675-3100 |
| FAMILY PRACTICE | CLINT BLACK | | |
| FAMILY PRACTICE | HUMPHREY BOGART | 17190 BERNARDO CENTER DR. SAN DIEGO, | 619-675-3100 |
| PEDIATRICS | JAMES BOND | 17190 BERNARDO CENTER DR. SAN DIEGO, | 619-675-3100 |
| FAMILY PRACTICE | HILARY CLINTON | | |
| INTERNAL MEDICINE | HARRY CONNICK, JR. | 17190 BERNARDO CENTER DR. SAN DIEGO, | 619-675-3100 |
| FAMILY PRACTICE | DENNIS CONNORS | | |
| FAMILY PRACTICE | HARRISON FORD | 17190 BERNARDO CENTER DRIVE SAN DIEGO | 619-675-3100 |
| FAMILY PRACTICE | CLARK GABLE | 17190 BERNARDO CENTER DR. SAN DIEGO, | 619-675-3100 |
| FAMILY PRACTICE | BILL GATES | 17190 BERNARDO CENTER DR. SAN DIEGO, | 619-675-3100 |
| FAMILY PRACTICE | KATHERINE HEPBURN | 17190 BERNARDO CENTER DR. SAN DIEGO, | 619-675-3100 |
| SPECIAL DISEASES | MARTINA HINGIS | | |
| FAMILY PRACTICE | VAL KILMER | 17190 BERNARDO CENTER DR. SAN DIEGO, | 619-675-3100 |
| INTERNAL MEDICINE | JAY LENO | 17190 BERNARDO CENTER DR. SAN DIEGO, | 619-675-3100 |
| SPECIAL DISEASES | DAVID LETTERMAN | 17190 BERNARDO CENTER DR. SAN DIEGO, | 619-675-3100 |
| INTERNAL MEDICINE | JERRY LEWIS | 17190 BERNARDO CENTER DR. SAN DIEGO, | 619-675-3100 |
| SPECIAL DISEASES | MARK MCGUIRE | | |
| URGENT CARE | NATALIE MERCHANT | 17190 BERNARDO CENTER DR. SAN DIEGO, | 619-675-3100 |

FIG. 36

| MAIN MENU | DUPLICATE ENTRY | NEW ENTRY | FIND | SORT |

DRUGS AND THERAPEUTIC CLASSES AS OF 2/13/00 — 2602

2604

| CLASS# | THERAPEUTIC CLASS NAME | DRUG NAME FORMAT TO APPEAR ON REPORTS | NDC CODE | DRUG NAME LINKED BY |
|---|---|---|---|---|
| 152100 | ALLERGY | ATROVENT 0.03% SPRAY | 000597008130 | |
| 072000 | ALLERGY | ATROVENT 0.06% SPRAY | 00597008676 | |
| 072000 | ALLERGY | ATROVENT 18.00 AERS | 00597008214 | |
| | ALLERGY | ATROVENT INH 18MCG/AC AER | | |
| | ALLERGY | ATROVENT INHAL SOL | | |
| 072000 | ALLERGY | ATROVENT INHALER | | |
| 072000 | ALLERGY | ATROVENT NAS 0.0003 SOL | | |
| 152100 | ALLERGY | ATROVENT NASAL | | |
| 072000 | ALLERGY | ATROVENT REF 18MCG/AC AER | | |
| 152100 | ALLERGY | VANCENASE 42.00 AERS | 00085064902 | |
| 152100 | ALLERGY | VANCENASE 42MCG | | |
| 152100 | ALLERGY | VANCENASE 42MCG INHALER | 00085004106 | |
| 152100 | ALLERGY | VANCENASE AQ .084% DS SPR | | |
| 152100 | ALLERGY | VANCENASE AQ 84MCG | | |
| 152100 | ALLERGY | VANCENASE NA PKTHALER AER | | |
| | ALLERGY | VANCENASE POCKETHALER 7 G | | |
| | BETA AGONIST | ACETYLCYSTEINE | | |
| | BETA AGONIST | AEROBID 250.00 AERS | | |
| | BETA AGONIST | AEROBID 250MCG AER | | |
| | BETA AGONIST | AEROBID AEROSOL W/ADAPTER | | |
| | BETA AGONIST | AEROBID-M 250MCG AER | | |
| | BETA AGONIST | AEROBID-M AEROSOL W/ADAPTER | | |
| 151100 | BETA AGONIST | ALBUTEROL 0.00083 NEB | | |
| 151100 | BETA AGONIST | ALBUTEROL 0.005 NEB | | |
| 151100 | BETA AGONIST | ALBUTEROL 0.08% NEB | | |
| 151100 | BETA AGONIST | ALBUTEROL 0.08 NEBU | 59930150006 | |

FIG. 37

PHARMATRAK

PATIENT LIST AS OF 2/13/00

| 2810<br>PATIENT FULL NAME | 2812<br>SUBS. SSN | 2802<br>2814<br>GROUP ID | 2816<br>PROVIDER ID | 2818<br>INSURANCE PLAN |
|---|---|---|---|---|
| ABIOG, ALBERT | | | | |
| ABRAMS ,FRANK D | 3651 | | | |
| ALABACK, JEAN | 3601 | | | |
| ALCALA ,SHEILA L | 5450 | | | |
| ALLISON ,DELLA S | 0 | | | |
| AMBURGEY, SAMUEL | 4773 | | | |
| AMBURGEY, SHIRLEY | 3821 | | | |
| ANDERSON ,DEBORAH | 5344 | | | |
| ANDERSON ,KEITH R | 5344 | | | |
| ANDERSON ,MAUREEN | 0 | | | |
| ANDRESS, EDWIN | | | | |
| APPLEBY ,DOROTHY J | 0 | | | |
| APRILE ,MARY | 5616 | | | |
| BAKER ,JEAN S | 0 | | | |
| BALKIN ,BETTY R | 0 | | | |
| BALKIN ,MAX | 0 | | | |
| BENNETT ,LOIS J | 0 | | | |
| BERG, SHIRLEY | | | | |
| BERMAN, LORI | 5580 | | | |
| BETTS ,ELMER F | 4971 | | | |
| BIGELOW ,HERBERT G | 0 | | | |
| BLACK ,WILLADEAN E | 5491 | | | |
| BOEGLIN ,SANDRA A | 5578 | | | |
| BRACKEY ,MURIEL P | 0 | | | |
| BRETL ,MARGARET | 0 | | | |
| BROOKS ,ALAN L | 0 | | | |
| BROOKS ,MOLLY A | 0 | | | |

FIG. 39     2800

PRESCRIPTION FORM

PHARMATRAK
THE PHARMACY BENEFIT MANAGEMENT SOFTWARE

- Date Filled
- Therapeutic Class
- Drug Name
- Days Supply
- Dosage Form
- Metric Qty.
- Strength
- Brand_Generic
- Generic name
- New or Refill Code
- Formulary Status
- NDC Code
- Prescription #
- Calc Ingredient Cost
- AWP Cost
- Copay Amount
- Dispensing Fee
- Paid Amount
- Physicians DEA #
- Phys First Name
- Phys Initial
- Phys Last Name
- Medical Group Name
- Medical Group Clinic
- Network
- Pharmacy ID
- Pharmacy Name
- Patient Name
- Patient Sex    Patient Age  0
- Patient DOB
- Patient SSN
- Member ID    Mbr Relation Code

- Insurance Plan  Health Net
- Group ID
- Paid Date
- Disease State
- HIV Drugs
- DAW
- AHFS
- Injectable
- Diabetic Indicator
- Anniversary Date
- Smoking Deterrant
- GPI
- Form Claim Flag
- risk Pool Claim Flag
- Diagnosis Code
- Submit Date of Claim
- usual customary
- Prior Auth Claim Flag
- Sales Tax
- Seq# of Claim
- Insulin
- Batch#
- Processor#
- PAMCSC#
- PAMCSC Code
- Wolf Cust Location
- Resubmission Cycle Count
- Dir Mbr Reimbursement
- Drug Compound

FIG. 40

PHARMACY BENEFIT MANAGEMENT SYSTEM AND METHOD OF USING SAME

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Technical Field

The present invention relates in general to a pharmacy benefit management system and method of using it. The invention more particularly relates to a system which facilitates the monitoring of prescriptions authorized by a medical group according to a novel method.

2. Background Art

The health provider system known as managed care was created to provide health care at a reasonable cost. Under managed care, subscribers of a health care plan received health care at reduced rate by controlling the health care costs of the entire pool of subscribers. One such health care plan was the health maintenance organization ("HMO") which controlled health care costs, in part, by contractual arrangement with individual physicians. In exchange for agreeing to provide health care services for the subscribers of the HMO, the physicians would be reimbursed by the HMO for the health care services provided.

In an effort to obtain more leverage in negotiating agreements with the HMOs, groups of physicians became associated with one another as medical groups. Such medical groups were formed as corporations, partnerships, and other associations to enable each physician in the medical group to obtain more patients, higher reimbursements, etc. from the HMOs than a single physician could obtain without the medical group.

A component of managed care was the capitation of a pharmacy benefit. The capitation referred to a fixed amount of money paid by the health care plan to the medical group to manage the costs of prescription drugs for subscribers of the health care plan (the patients of the medical group physicians). The amount paid by the health care plan was determined on a per subscriber, per month, basis. In the event the costs of drugs prescribed by the medical group are less than the capitation of the pharmacy benefit, the medical group realizes the difference between the capitation and the actual drug costs as a pharmacy benefit profit. However, if the costs of the prescribed drugs exceeds the capitation, the medical group was indebted to the health care plan for the difference between the actual drug costs and the capitation, and the medical group realized a pharmacy benefit loss.

It has been difficult to monitor the drugs actually prescribed by the physicians of the medical group to enable the medical group to identify the prescribing activity of the physicians to help predict the expected costs for the actual drug costs. Furthermore, the actual drug costs could not be determined with a high degree of certitude, since the costs for the drugs prescribed could vary, depending upon the pharmacy where the drugs were obtained by the patient. Consequently, the actual drug costs relative to the pharmacy benefit capitation could not be determined with any real accuracy for the small medical group.

Therefore, it would be highly desirable to have a new and improved pharmacy benefit management system which can enable a medical group to analyze actual drug costs relative to a pharmacy benefit capitation for managing prescription drug activity. Such a pharmacy benefit management system should be relatively inexpensive, and convenient to use.

Also, it has been difficult to monitor pharmacy claims received from the pharmacies supplying the prescription drugs to the patients. As a result, the medical group could not determine if the patients were obtaining the drugs actually prescribed by the medical group physicians. Without the pharmacy claim information, the medical group was unable to determine the drugs, and the actual costs of the drugs, actually obtained by the patients.

Therefore, it would also be highly desirable to have a pharmacy benefit management system which would provide information regarding the drugs obtained, and their actual costs, to the medical group based on the prescription activity of the medical group physicians.

SUMMARY OF THE INVENTION

Therefore, the principal object of the present invention is to provide a new and improved pharmacy benefit management system, and a method of using it, wherein a medical group is enabled to analyze actual drug costs and utilization rates by individual physicians and by the entire medical group relative to a pharmacy benefit capitation for managing prescription drug activity, in a relatively inexpensive manner and in a manner convenient to use.

Another object of the present invention is to provide such a pharmacy benefit management system which provides a medical group with information regarding the drugs obtained, and their actual costs, based on the prescription activity of the medical group physicians.

Briefly, the above and further objects of the present invention are realized by providing a new and improved pharmacy benefit management system which enables a medical group to monitor prescription utilization information for the medical group to enable the medical group to manage pharmacy costs relative to a pharmacy benefit capitation.

The pharmacy benefit management system includes a pharmacy computer for generating pharmacy claim information based on pharmacy activity of a medical group. A health plan computer is responsive to the pharmacy claim information for generating pharmacy activity information for the medical group. A medical group computer receives the pharmacy activity information from the health plan computer and stores the pharmacy activity information. The pharmacy activity information is processed to generate utilization information to enable the medical group to monitor the pharmacy activity.

BRIEF DESCRIPTION OF THE DRAWINGS

The above mentioned and other objects and features of this invention and the manner of attaining them will become apparent, and the invention itself will be best understood by reference to the following description of the embodiment of the invention in conjunction with the accompanying drawings, wherein:

FIGS. 15–40 are information screens and reports generated by the pharmacy benefit management software of FIGS. 2–14.

BEST MODE FOR CARRYING OUT THE INVENTION

Figure 1:
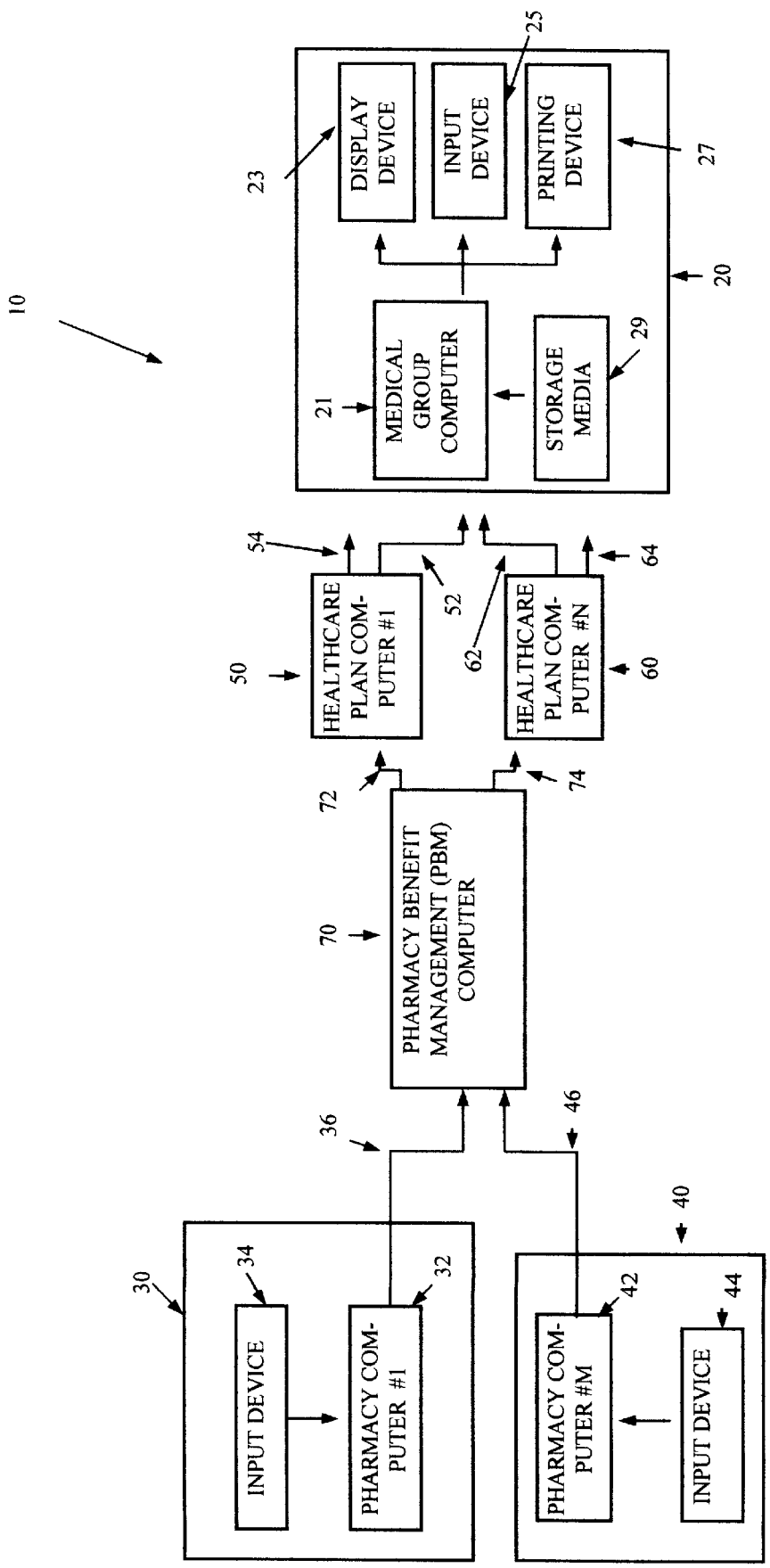
FIG. 1 is a block diagram of a pharmacy benefit management system, which is constructed in accordance with the present invention.

Referring now to the drawings, and more particularly to FIG. 1, thereof, there is shown a pharmacy benefit management system 10, which is constructed in accordance with the present invention. The system 10 can be used to monitor the pharmacy activity of a medical group 20 in accordance with the method of the present invention. The system 10 enables the medical group 20 to examine pharmacy claims data, to create reports regarding pharmacy activity, and to manage the utilization of pharmaceutical prescriptions made by physicians (not shown) belonging to the medical group 20.

The system 10 generally includes one or more pharmacy computers, such as pharmacy computers 32 and 42, which generate pharmacy claim information 36 and 46 when prescriptions are filled at their pharmacies, such as the respective pharmacies generally indicated at 30 and 40. The pharmacy claim information indicated generally at 36 and 46 includes prescribed drug information that corresponds to the prescription activity of the physicians of the medical group 20. One or more health care plan computers, such as health care plan computers 50 and 60, are responsive to the prescribed drug information, and generate medical group prescription information, such as medical group prescription information generally indicated at 52, 54, 62 and 64, for all participating medical groups.

A medical group computer 21 for the medical group 20 receives and stores the medical group prescription information 52 and 62 corresponding to the medical group 20. The medical group prescription information 52 and 62 is unformatted, raw data indicative of the pharmacy claims. The medical group prescription information 52 and 62 can be supplied directly to the medical group computer 21 by hard wire connections, by a telephone communication network, by portable storage media, or by any other suitable arrangement for communicating information between computers.

As hereinafter described in greater detail, the system 10 further includes pharmacy benefit management software for processing the medical group prescription information 52 and 62 to generate and present utilization information that is indicative of the prescription activity for the medical group 20. According to the invention, the medical group 20 is able to monitor the prescription activity relative to a pharmacy benefit capitation associated with the medical group 20 to determine if the prescription activity should be modified.

The system 10 further includes a pharmacy benefit management (PBM) computer 70 connected between the pharmacy computers 32 and 44, and the health care plan computers 50 and 60. The PBM computer 70 receives the pharmacy claim information 36 and 46 from the pharmacy computers 32 and 42, and accumulates the pharmacy claim information for submission to the appropriate health care plan computer, such as health care plan computers 50 and 60. Once the PBM computer 70 accumulates a sufficient amount of pharmacy claim information, the accumulated pharmacy claim information 72 and 74 is transmitted electronically to the appropriate health care plan computers 50 and 60. The health care plan computers 50 and 60 utilize the accumulated pharmacy claim information to facilitate approval of the pharmacy claims made by the pharmacies 30 and 40, and to facilitate the reimbursement of the pharmacies 30 and 40 for the prescription drugs supplied.

In operation, a physician belonging to the medical group 20 prescribes a drug for a subscriber or patient (not shown). The patient then obtains the prescribed drug from one of the pharmacies 30 and 40. Using input devices 34 and 44 to enter prescription information to the pharmacy computers 32 and 42, the pharmacy computers 32 and 42 generate the pharmacy claim information 36 and 46 to facilitate obtaining reimbursement from the patient's health care plans for the drugs dispensed by the pharmacies 30 and 40.

The pharmacy claim information 36 and 46 is accumulated by the PBM computer 70 to facilitate the approval of the pharmacy claims for reimbursement by the health care plans. The accumulated pharmacy claim information 72 and 74 is transmitted electronically to the health care plan computers 50 and 60, wherein the accumulated pharmacy claim information 72 corresponds to prescriptions for patients subscribing to the health plan associated with the health care plan 50, and the accumulated pharmacy claim information 74 corresponds to pharmacy claims for patients subscribing to the health plan associated with the health care plan computer 60.

The health care plan computers 50 and 60 analyze the accumulated pharmacy claim information 72 and 74 to determine if reimbursement for the pharmacy claims is appropriate. If reimbursement is appropriate, the health care plan computers 50 and 60 facilitate the reimbursement of the pharmacies 30 and 40 for the approved pharmacy claims.

Once the pharmacy claims are approved by the health care plan computers 50 and 60, the medical group prescription information 52, 54, 62, and 64 is transmitted to the corresponding medical group by a suitable arrangement, wherein the medical group prescription information 52 and 62 corresponds to the medical group 20. The medical group prescription information 52 and 62 is unformatted, raw data indicative of the pharmacy activity of the medical group 20.

The medical group prescription information 52 and 62 is transmitted to the medical group computer 21 for processing to generate utilization information indicative of the pharmacy activity. Under the control of the pharmacy benefit management software described hereinafter in greater detail, the medical group computer 21 enables the medical group 20 to monitor the pharmacy activity. In this way, the pharmacy activity can be compared to an appropriate pharmacy benefit capitation to determine if the medical group 20 is incurring a pharmacy benefit loss or a pharmacy benefit profit, and reports can be generated as hereinafter explained in greater detail. Based upon the utilization information, the pharmacy activity can be modified to ensure the medical group 20 is incurring a pharmacy benefit profit.

Considering now the medical group 20 in greater detail, the medical group 20 further includes a display device 23 connected to the medical group computer 21 for providing a visual indication of the utilization information. An input device 25, such as a keyboard or a mouse, facilitates interacting with the pharmacy benefit management software. A printing device 27 coupled to the medical group computer 21 enables the utilization information to be printed. A storage media 29 stores the pharmacy benefit management software, and cooperates with the medical group computer 21 to enable the pharmacy benefit management software to help process the medical group prescription information 52 and 62.

Referring now to FIGS. 2–14, there are shown flow charts illustrating the operation of the pharmacy benefit management software. The software enables the medical group prescription information 52 and 62 (FIG. 1) to be processed for identifying patterns of utilization for the medical group 20 (FIG. 1); identifying problem areas for the medical group 20; and for creating treatment guidelines based on disease states to improve the management of the disease state and to set standards for pharmaceutical utilization.

The progress of the medical group 20 is also monitored over time, and report cards identifying patterns of utilization for individual physicians are created.

Focused educational programs are implemented to encourage appropriate pharmaceutical utilization, and feedback is provided to the physician over time to modify prescribing behavior.

Script information illustrating the operation of the software is attached hereto as Appendixes A, B, C, D and E. Appendix A is directed to the main or prescription data file. Appendix B is directed to a patient or subscriber file. Appendix C is directed to a physician file. Appendix D is directed to a member month's file. Appendix E is directed to a therapeutic class file.

Considering the software stored in the storage media 29 in greater detail with reference to FIGS. 2–14, there is shown a main organization flow chart 100 (FIG. 2) for determining the type of evaluation to be performed on the medical group prescription information 52 and 62 (FIG. 1). A main menu 110 is presented wherein the available selections are physician reports 112, medical group reports 114, miscellaneous reports 116, prescription form information 118, physician information 120, patient information 122 and therapeutic class information 124.

Figure 2:
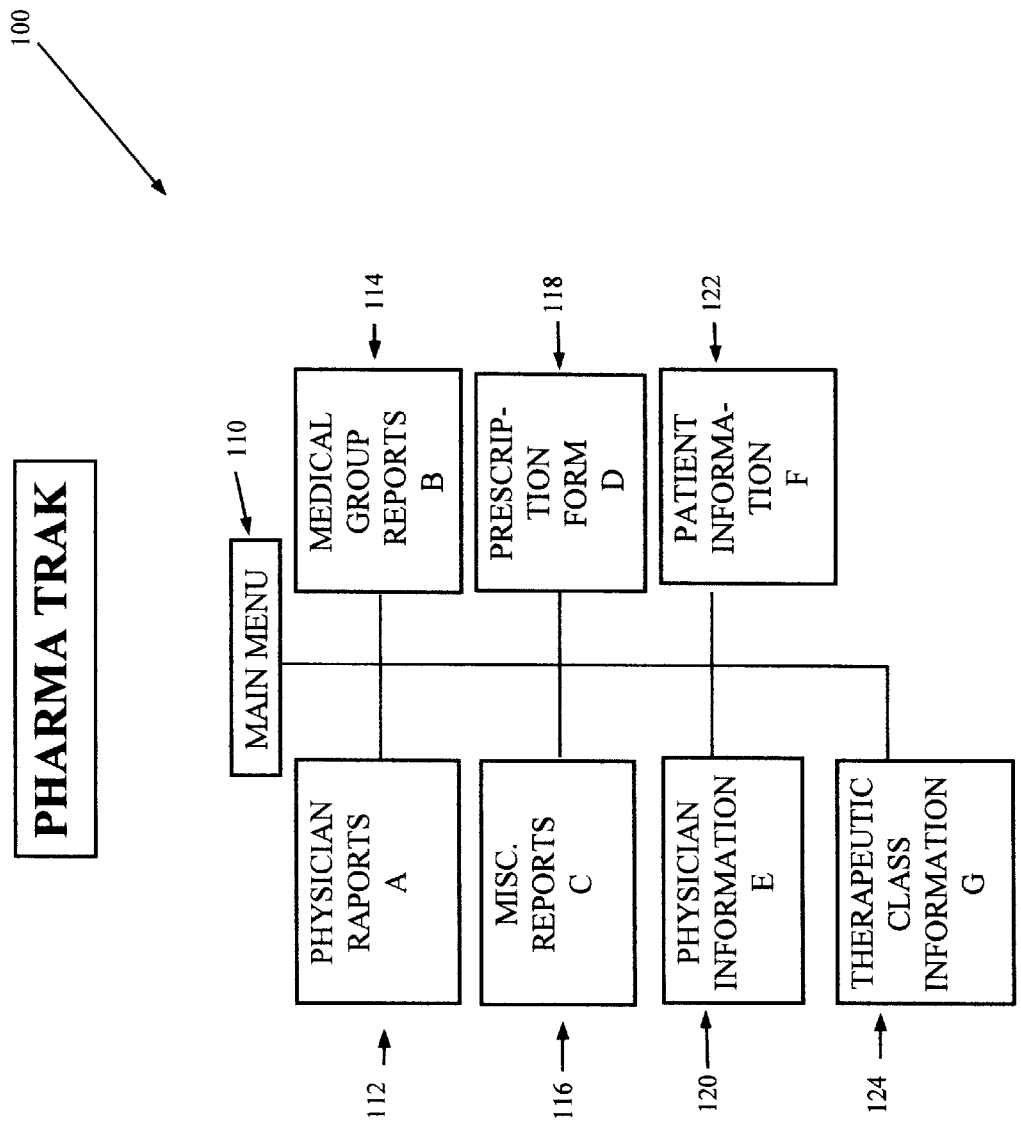
FIGS. 2–14 are flow charts illustrating the operation of pharmacy benefit management software of the pharmacy benefit management system of FIG. 1.
Figure 3:
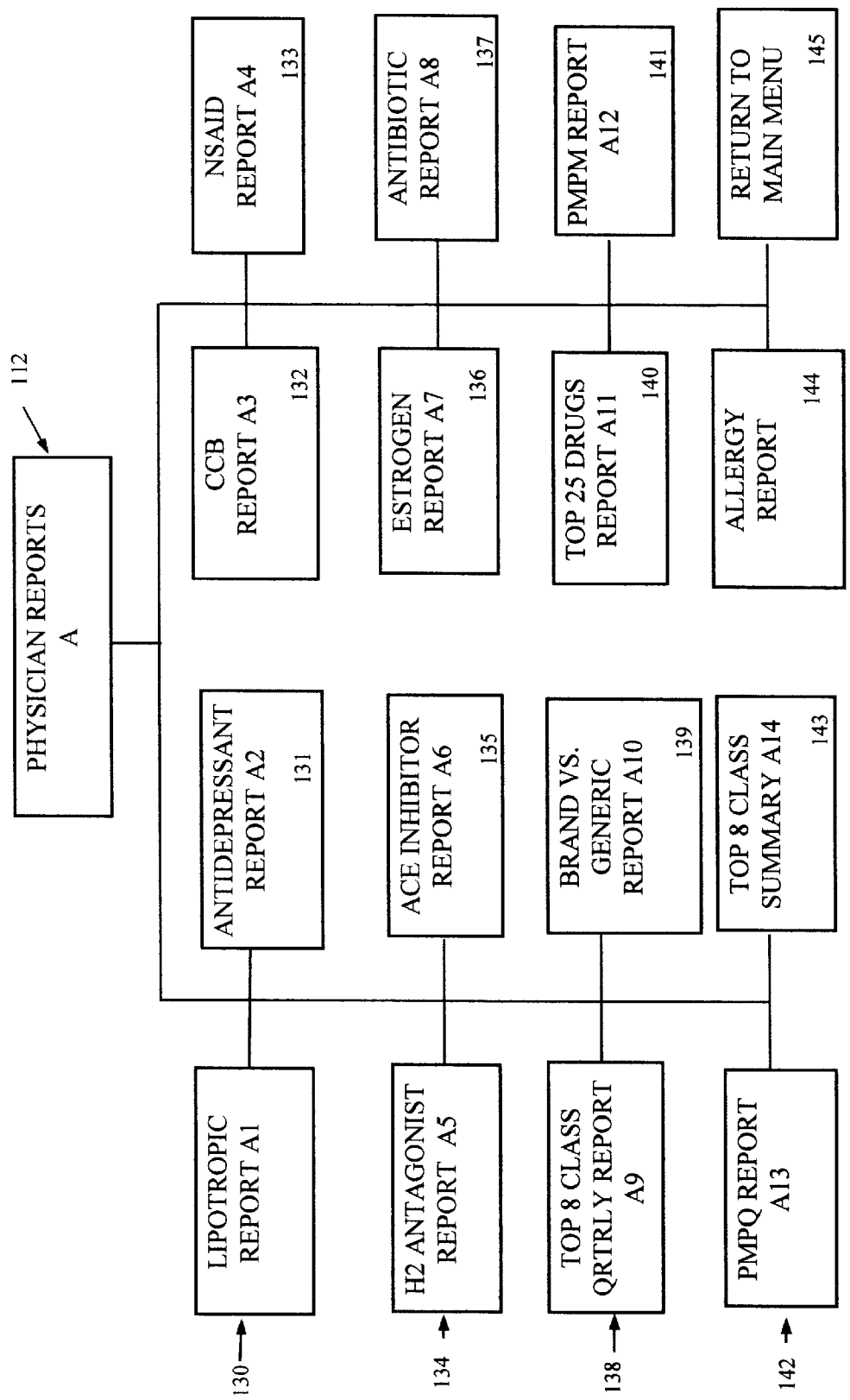

As shown in FIG. 3, the selection of physician reports 112 (FIG. 2) enables the utilization information to be presented in a variety of report formats, including a lipotropic report 130, an antidepressant report 131, a CCB report 132, an NSAID report 133, an H2 antagonist report 134, an ACE inhibitor report 135, an estrogen report 136, an antibiotic report 137, a top 8 class quarterly report 138, a brand vs. generic report 139, a top 25 drugs report 140, a PMPM report 141, a PMPQ report 142, a top 8 class summary 143, and an allergy report 144. The main menu 110 can be presented again at box 145.

Figure 4:
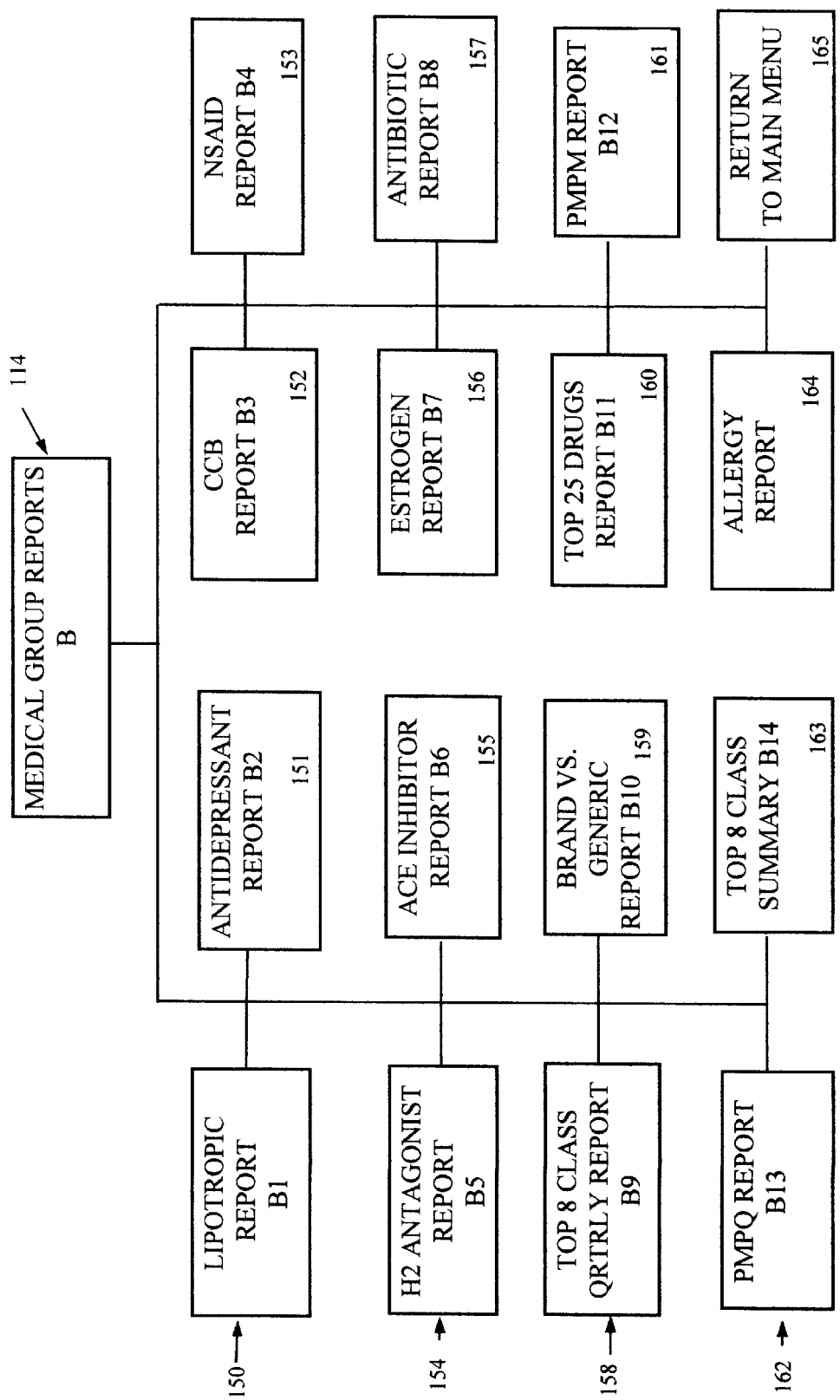

As shown in FIG. 4, the selection of the medical group reports 114 (FIG. 2) enables the utilization information to be presented in reports substantially similar to the physician reports 112 of FIG. 3. In this regard, the medical group reports 114 facilitates presenting the utilization information according to the following formats: A lipotropic report 150; an antidepressant report 151; a CCB report 152; an NSAID report 153; an H2 antagonist report 154; an ACE inhibitor report 155; an estrogen report 156; an antibiotic report 157; a top 8 class quarterly 158; a brand vs. generic report 159; a top 25 drugs report 160; a PMPM report 161; a PMPQ report 162; a top 8 class summary 163; and an allergy report 164. The main menu 110 can be presented again at box 165.

Figure 5:
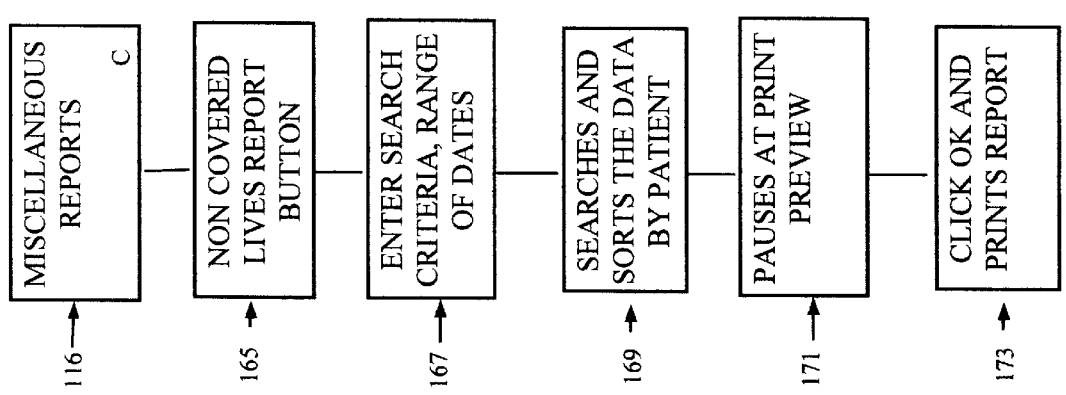

The selection of the miscellaneous report 116 (FIG. 2) enables other formats to be displayed as shown in FIG. 5. After selecting the miscellaneous report 116, a non covered lives report button 165 can be selected. Search criteria, including a range of dates is then selected at box 167. The utilization information is searched and sorted according to the patient at box 169. A preview of the printed report is displayed at box 171, and the report is printed at box 173 if the report is satisfactory.

Figure 6:
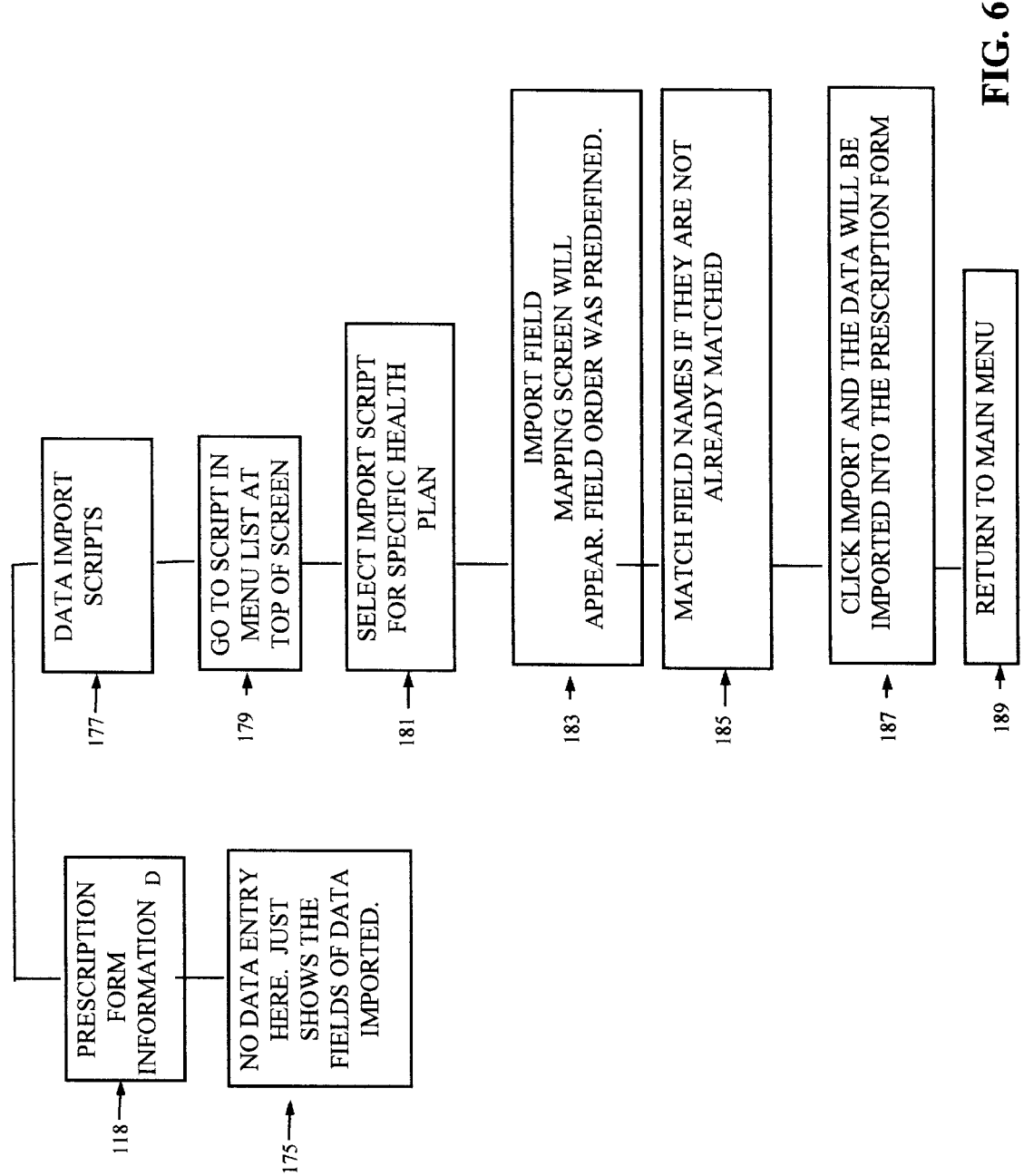

As shown in FIG. 6, selection of the prescription form information 118 (FIG. 2) enables the medical group prescription information 52 and 62 (FIG. 1) to be used. Upon selecting the prescription form information 118, a form field indicating data to be imported is displayed at box 175. The prescription form information 118 cooperates with data import scripts at box 177 to import the prescription information indicative of the pharmacy activity for the medical group 20 (FIG. 1). A script selection is selected at box 179, wherein the appropriate import script is selected for a particular health plan at box 181. An import field mapping screen is displayed at box 183, wherein the field order is predefined. Where field names are not appropriately matched, the field names are matched at box 185. Selecting the import function at box 187 enables the medical group prescription information 52 and 62 (FIG. 1) to be imported into a prescription form at box 187. The process is returned to the main menu 110 (FIG. 2) at box 189.

Figure 7:
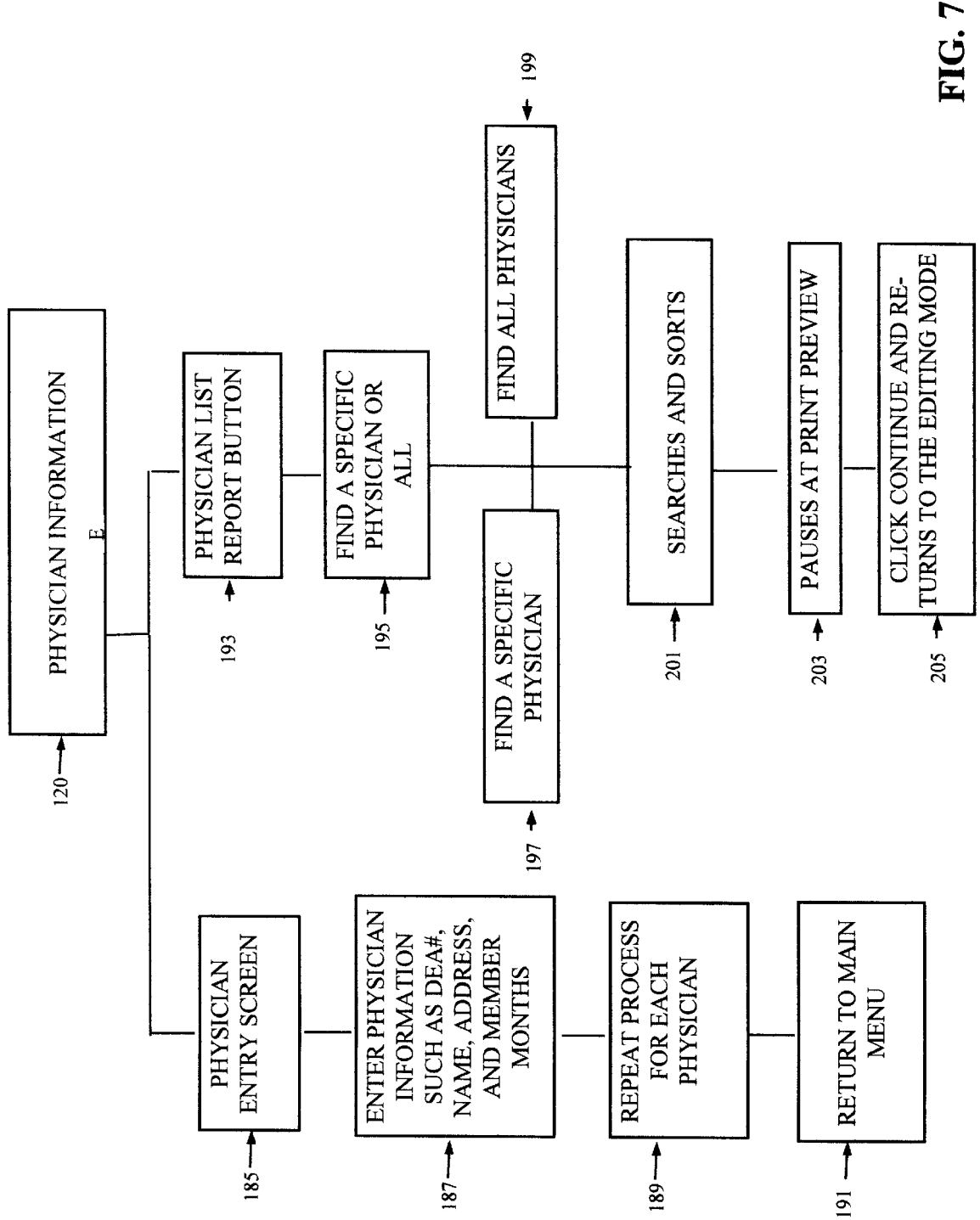

When the physician information 120 (FIG. 1) is selected from the main menu 110, the physician information 120 enables physician information to be entered or to be arranged and printed as shown in FIG. 7. Physician information is entered via a physician entry screen at box 185. Physician information, such as DEA No., name, address and member months information is entered at box 187. The entry of physician information is repeated at box 189 for each physician. When completed, the process is returned to the main menu 110 (FIG. 2) at box 191.

To prepare a list report of physicians, a physician list report button is selected at box 193. A particular physician, or all of the physicians, are selected for the report at box 195. For both the specific physician selection 197 and the all physician section 199, the utilization information is searched and sorted at box 201. A proposed report is displayed at box 203 for preview purposes. Further changes to the list can be made at box 205 before turning to an editing mode.

Figure 8:
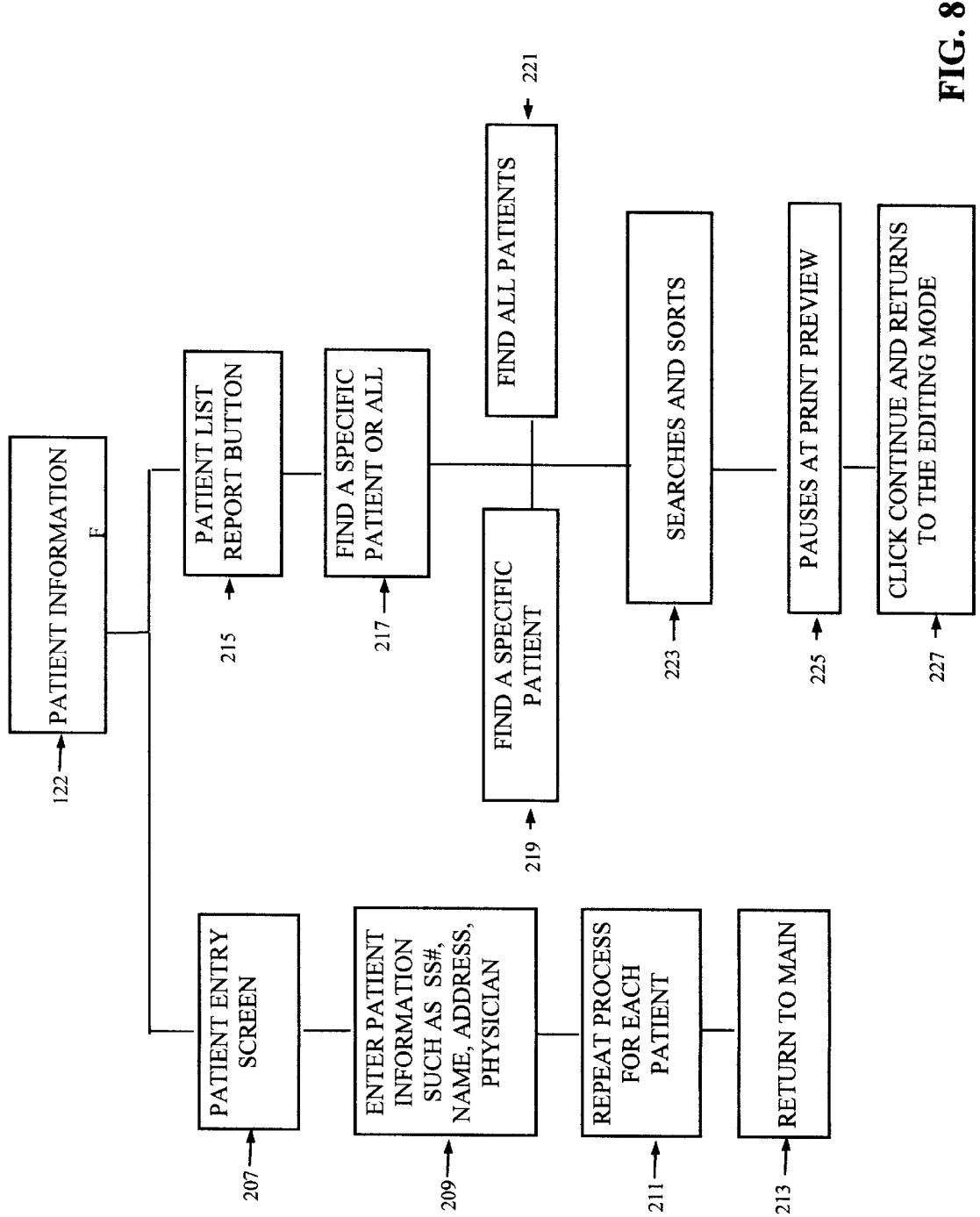

As shown in FIG. 8, the selection of the patient information 122 (FIG. 2) enables patient information to be entered, and enables a patient list report to be prepared. To enter patient information, the patient selection screen is selected at box 207. Patient information, including social security number, name, address and physician information is entered at box 209. The entry of patient information is repeated for each patient at box 211. Upon completion of the entry of the patient information, the process is returned to the main menu on 10 (FIG. 2) at box 213.

A patient list report is prepared by selecting a patient list report button at box 215. A determination is made at box 217 to prepare a report for a specific patient or for all patients at box 217. For both specific patient reports 219 and all patient reports 221, the patient and date information is searched and sorted at box 223. The resulting information is displayed at box 225, and further editing is enabled at box 227.

Figure 9:
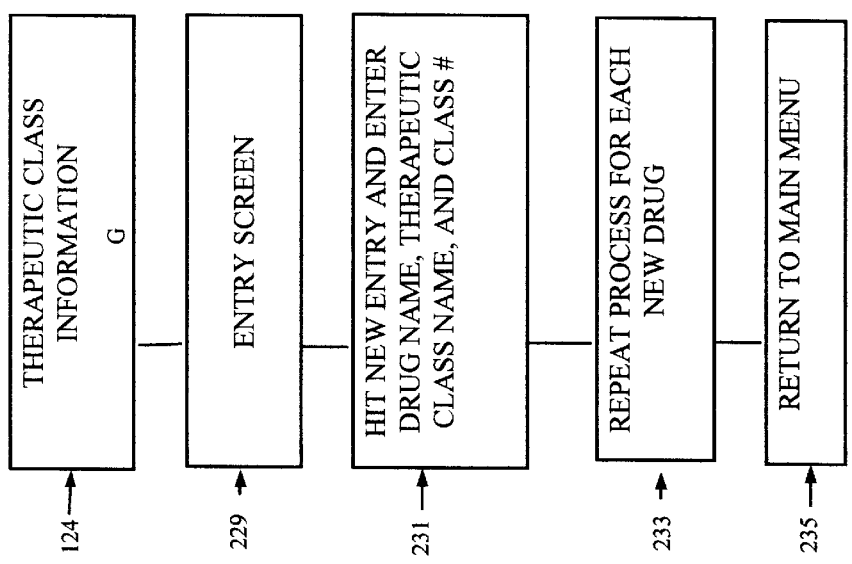

As best shown in FIG. 9, the selection of the therapeutic class information 124 (FIG. 2) enables information for additional drugs to be entered. In this regard, an initial entry screen is displayed at box 229. The drug name, therapeutic class name and class number are entered at box 231. The entry of drug information is repeated for each new drug at box 233, before the process returns to the main menu 110 (FIG. 2) at box 235.

Figure 10:
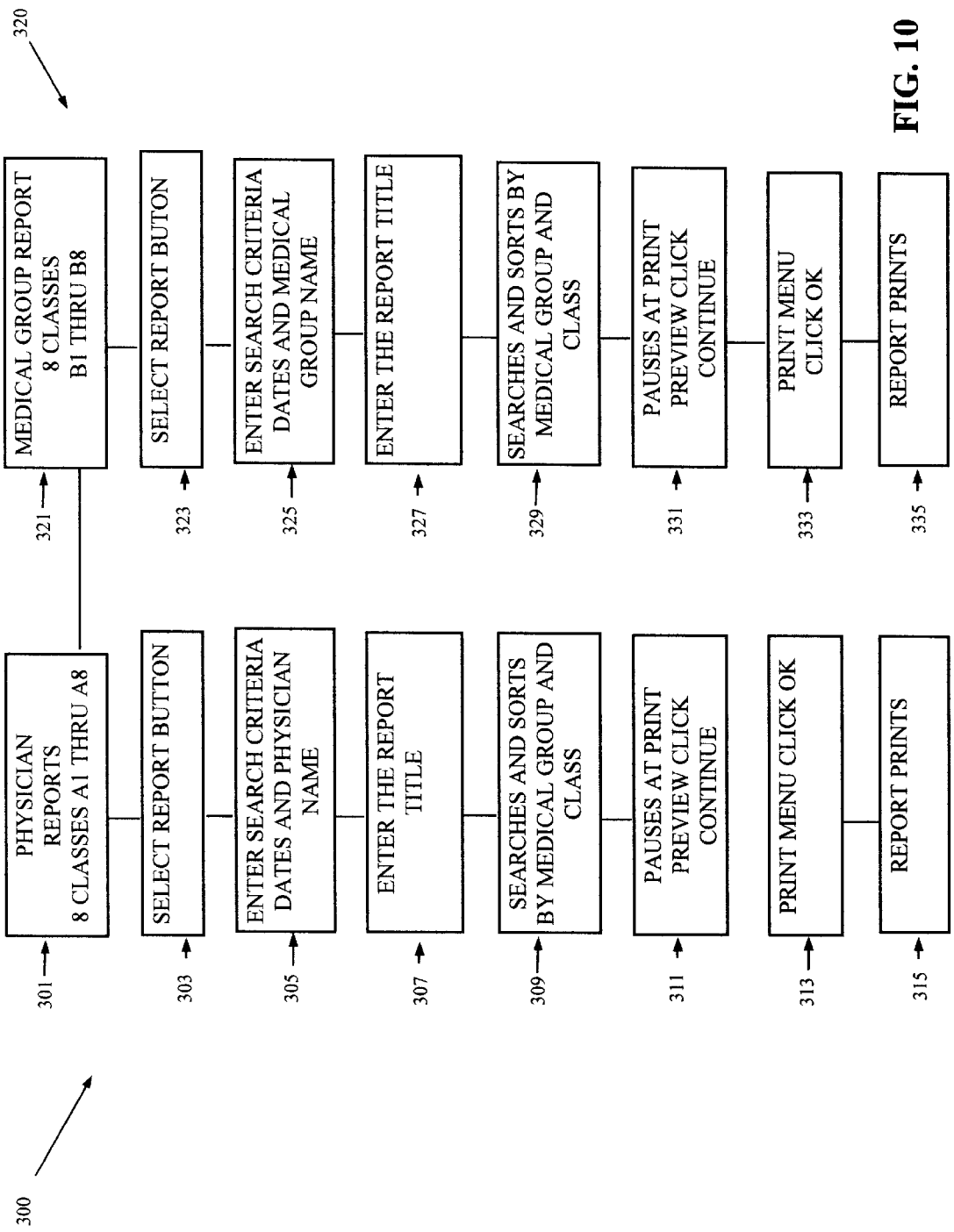

Considering now the physician reports 112 (FIG. 3) in greater detail, the report formats 130, 131, 132, 133, 134, 135, 136 and 137 are generated according to a physician report flow chart 300 (FIG. 10). Once it is determined that a physician report for the reports 130–137 is desired at box 301, a report button is selected at box 303. Search criteria including dates and physician name are entered at box 305. The report title is entered at box 307. The utilization information is searched and sorted according to medical group and class at box 309. The resulting information is displayed at box 311 for print preview purposes. If it is determined at box 313 that the information is acceptable, the printing of the report is initiated at box 315.

The preparation of medical group reports in response to the medical group selection 114 (FIG. 4) is substantially similar to the physician report flow chart 300. The medical group report flow chart 320 enables the formatting of the various medical group report types, including reports 150–157. After the desired report type is determined at box 321, the report button is selected at box 323. Search criteria, including dates and medical group name are entered at box 325. A title for the report is then entered at box 327.

The utilization information is searched and sorted according to medical group and class at box 329. The resulting information is displayed for preview purposes at box 331. If it is determined at box 333 that the desired information is acceptable, the report is printed at box 335.

Figure 11:
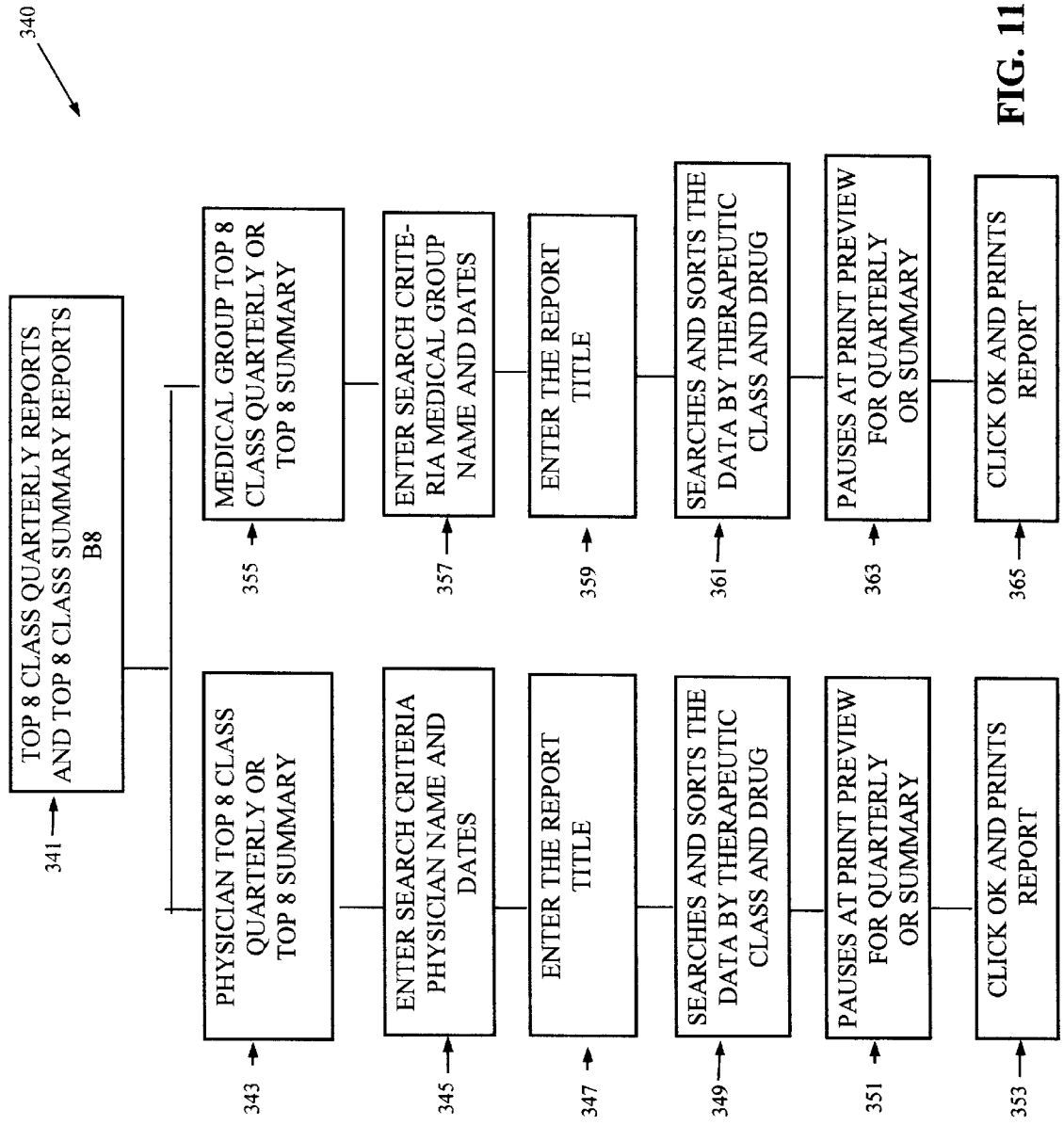

The top 8 class quarterly reports 138 (FIG. 3) and 158 (FIG. 4) and the top 8 class summary report 143 (FIG. 3) and 163 (FIG. 4) are generated according to the class flow chart 340 (FIG. 11). In this regard, the particular report format 138, 143, 158, or 163 is selected at box 341. The physician report formats 138 and 143 (FIG. 3) are selected at box 343 (FIG. 11). Search criteria, including the physician's name and date information are entered at box 345. A title for the report is selected at Box 347. The information is searched and sorted according to therapeutic class and drug at box 349. The searched and sorted information is displayed at box 351, and acceptance of the searched and sorted information is facilitated at box 353 to print the report.

The medical group report formats 158 and 163 (FIG. 4) are selected at box 355. Search criteria, including medical group, name and date information are entered at box 357. A title for the report is entered at box 359, and the information is subsequently searched and sorted according to therapeutic class and drug at box 361. The resulting information is displayed at box 363 for print preview purposes, and acceptance of the displayed information is indicated at box 365 to print the report.

Figure 12:
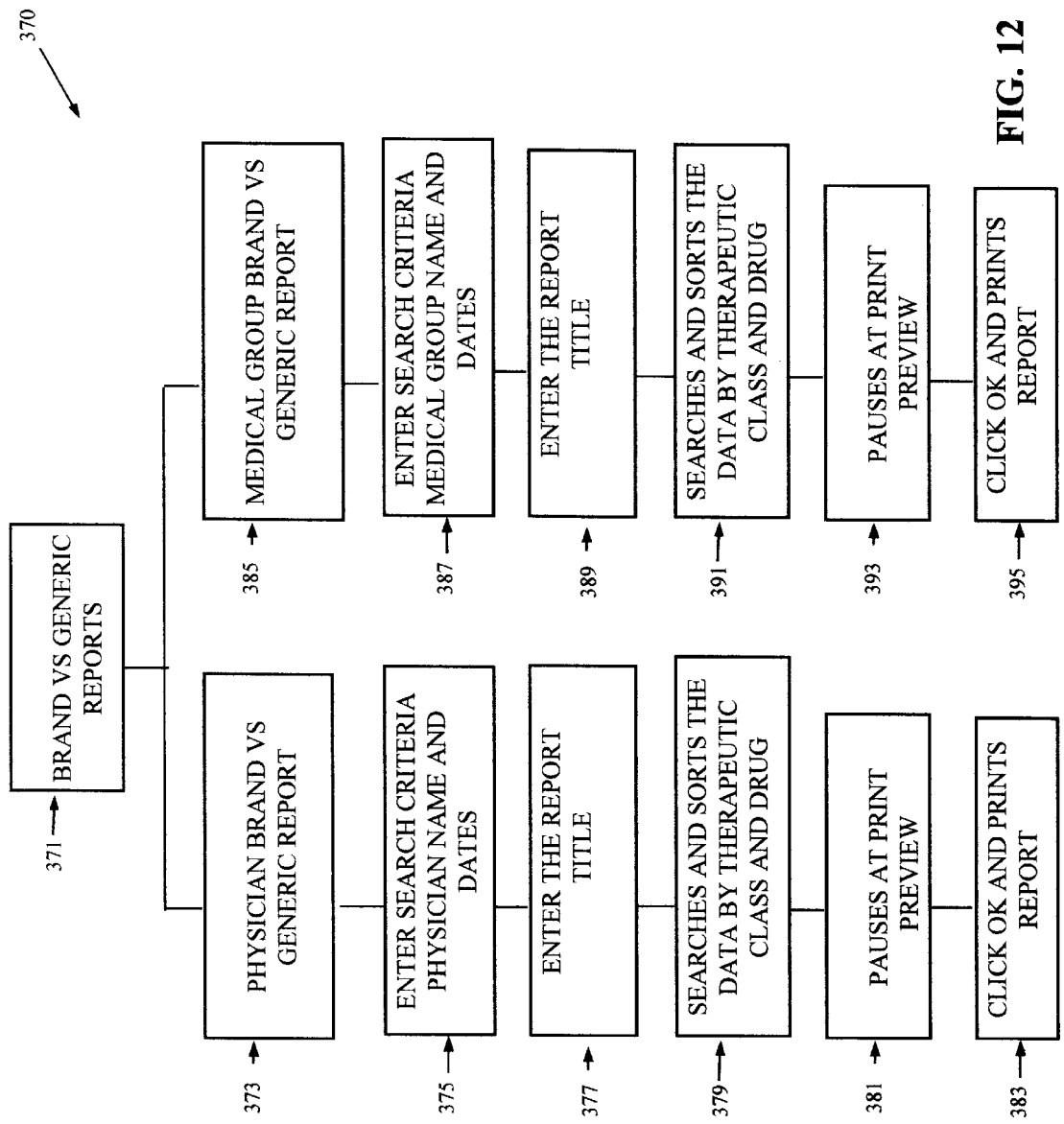

As seen in FIG. 12, the brand vs. generic report format 139 (FIG. 3) and 159 (FIG. 4) are determined according to the brand/generic flow chart 370. Initially, it is determined at box 371 that a brand vs. generic report is desired. The physician brand vs. generic format is initiated at box 373. Search criteria, including the physician's name and date information are entered at box 375. A title for the report is entered at box 377, and the information is searched and sorted according to therapeutic class and drug at box 379. The resulting information is displayed at box 381 for print preview purposes, and the report is accepted at box 383 to cause the report to be printed.

The medical group brand vs. generic report format is initiated at box 385. Search criteria including medical group name and date information is entered at box 387, and a title for the report is entered at box 389. The information is searched and sorted according to therapeutic class and drug at box 391, and the resulting information is displayed at box 393. If the displayed information is acceptable, the report is printed at box 395.

Figure 13:
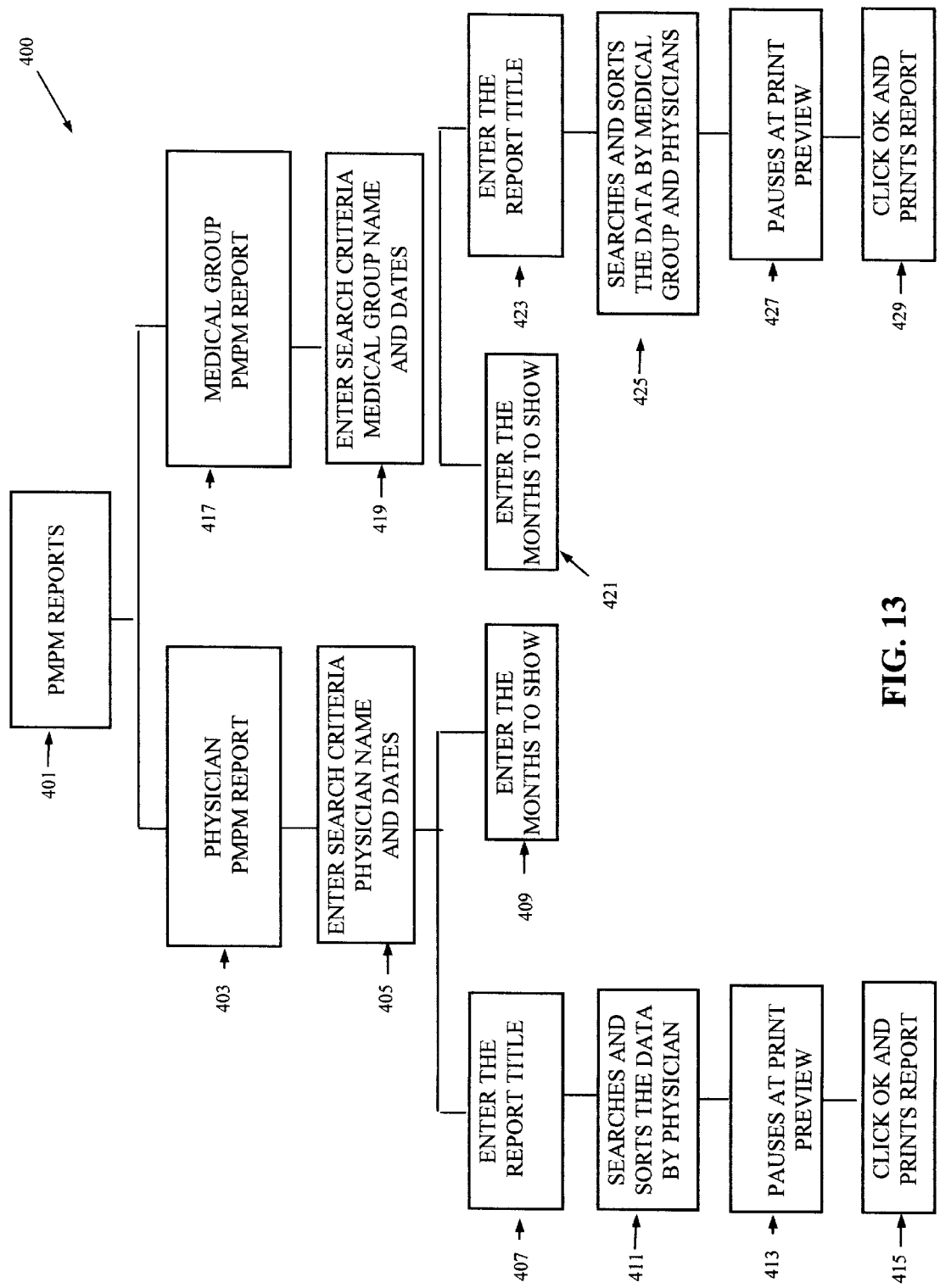

As seen in FIG. 13, the physician PMPM report format 141 (FIG. 3) and the medical group PMPM report format 161 (FIG. 4) are prepared according to the PMPM flow chart 400. The desire to prepare a PMPM report is detected at box 401. The selection of a physician PMPM report format is accomplished at box 403. Search criteria, including physician name and date information is named at box 405. The title to the report is entered at box 407, and the applicable months to show are selected at box 409. The information is searched and sorted according to the physician at box 411. The resulting information is displayed at Box 413, and if acceptable, the report is printed out at box 415.

The medical group PMPM report format is determined at box 417. Search criteria, including medical group name and date information is entered at box 419. The report title is entered at box 421, and the desired months to show are selected at box 423. The information is searched and sorted according to the medical group and physician at box 425. The resulting information is displayed for print preview purposes at box 427, and the report is printed out at box 429 if acceptable.

Figure 14:
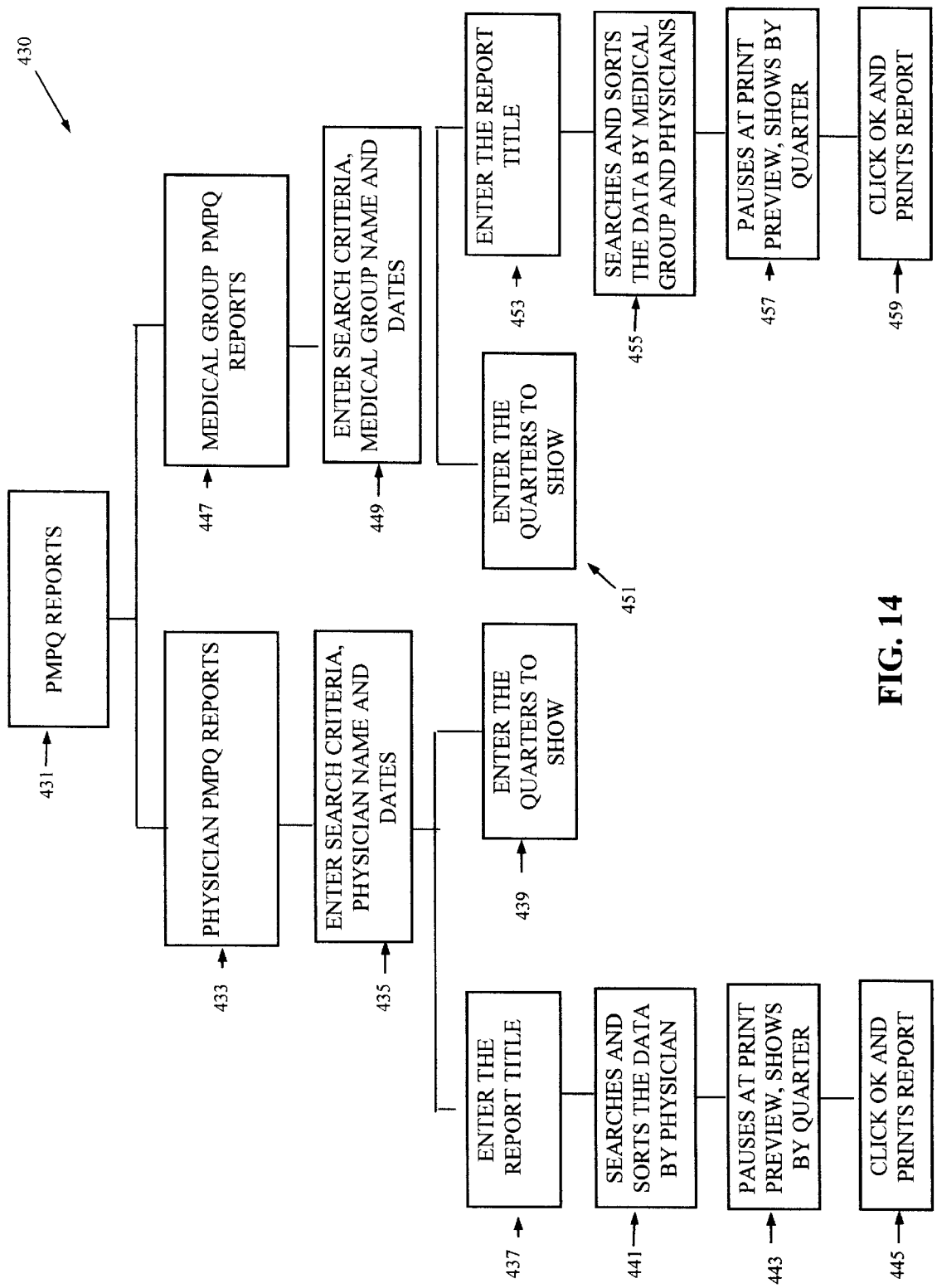

As seen in FIG. 14, the physician PMPQ report format 142 (FIG. 3) and the medical group PMPQ report format 162 (FIG. 4) are generated according to a PMPQ report flow chart 430. The physician and medical group PMPQ reports are initiated at box 431. The physician PMPQ report is initiated at box 433. Search criteria, including physician name and date information is entered at box 435. The report of the title is entered at box 437, and the desired quarters to be displayed at selected at box 439. The information is searched and sorted according to the physician at box 441. The resulting information is displayed at box 443, wherein the report is printed at box 445 if desired.

The medical group PMPQ report is initiated at box 447. Search criteria including medical group, name and date information is entered at box 449. The report title is entered at box 451, and the desired quarters to display are entered at box 453. The information is searched and sorted according to the medical group and physician at box 455. The resulting information is displayed by quarter at box 457, and the report is printed at box 459 if desired.

Figure 15:
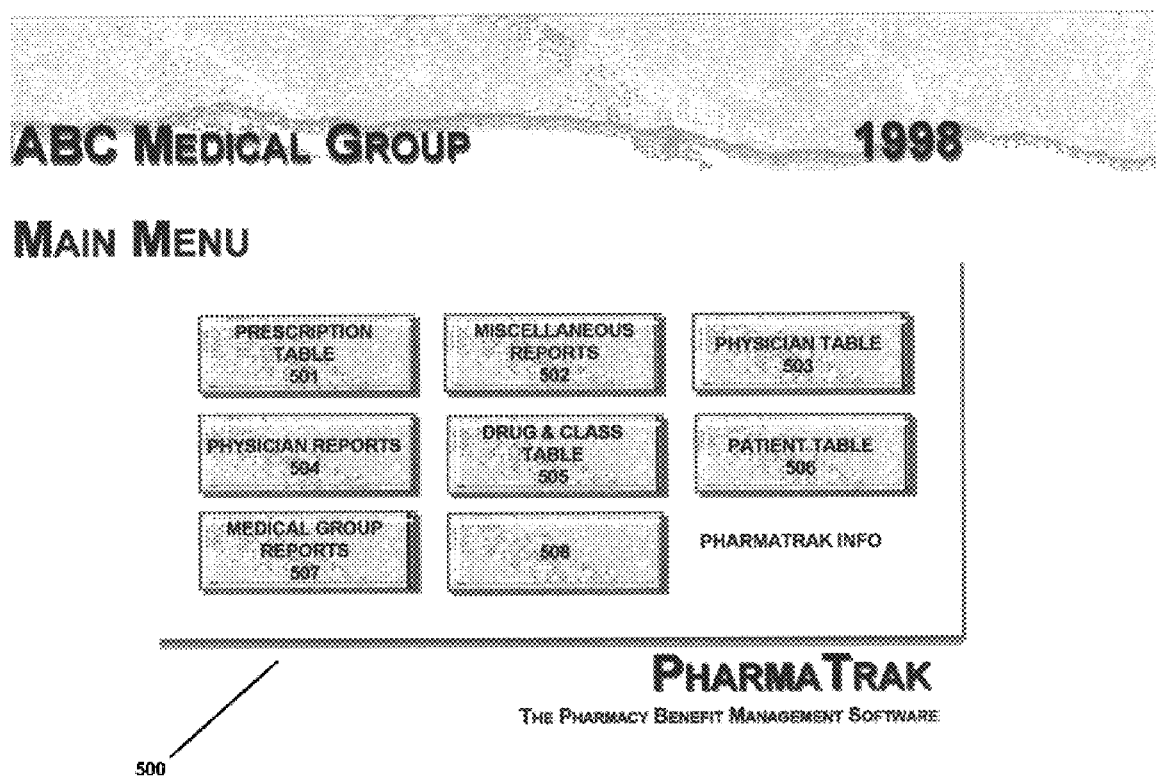
Figure 16:
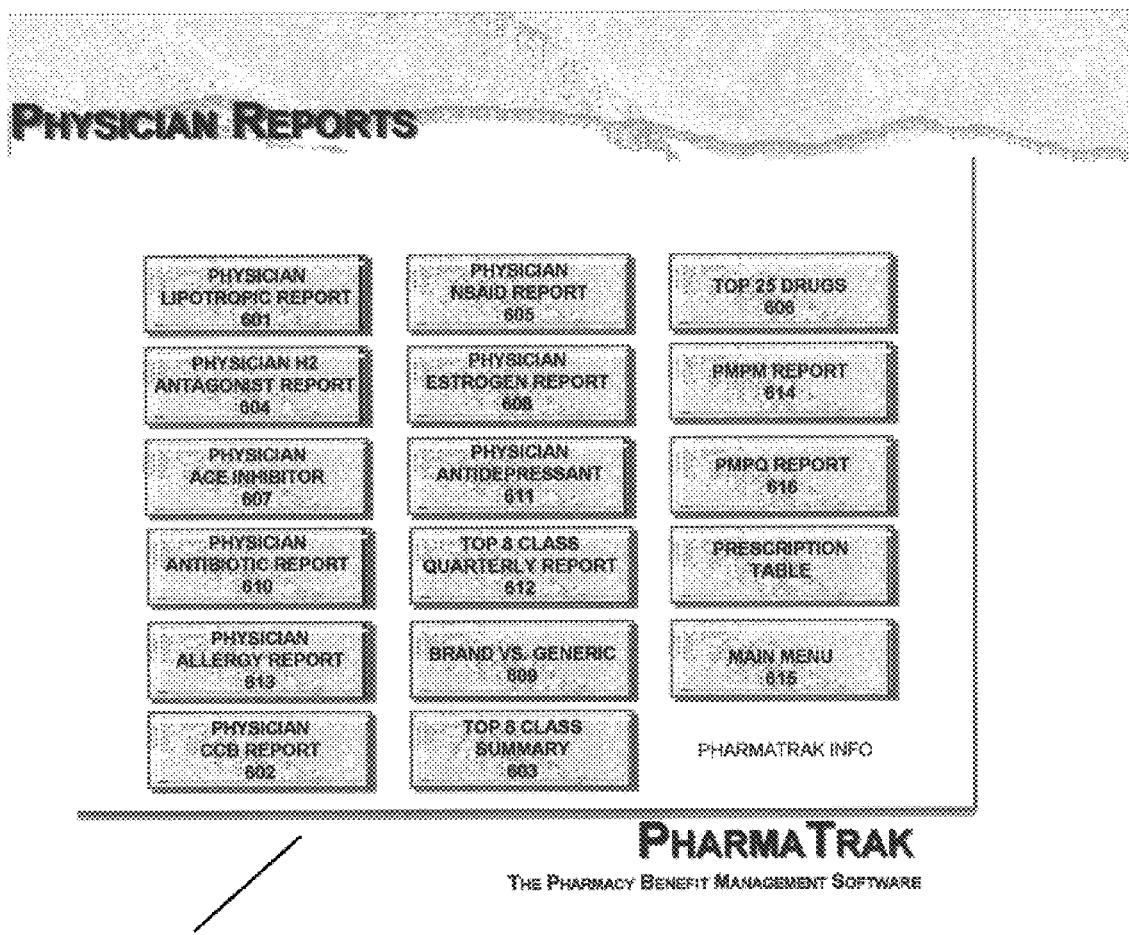

Referring now to FIGS. 15–40, there are shown information screens and reports generated by the pharmacy benefit management system 10 (FIG. 1), in accordance with the present invention. A main menu screen 500 is shown in FIG. 15. The main menu screen 500 corresponds to the main menu selection 110 (FIG. 2), and includes a plurality of buttons for generating desired reports, including a prescription forms button 501, a miscellaneous reports button 552, an update physician information button 503, a physician reports button 504, an update therapeutic class information button 505, an update patients button 506, a medical group reports button 507, and an additional unspecified button 508. The buttons 501–507 correspond substantially to the formats 118, 116, 120, 112, 124, 122, and 114 (FIG. 2).

Upon the selection of the physician reports button 504, a physician reports menu 600 (FIG. 16) is displayed. The physician reports menu 600 includes a plurality of buttons for selecting desired reports, including a physician lipotropic report button 601, a physician CCB report button 602, a top 8 class summary report button 603, a physician H2 antagonist report button 604, a physician NSAID report button 605, a top 25 drugs report button 606, a physician ACE inhibitor report button 607, a physician estrogen report button 608, a brand vs. generic report button 609, a physician antibiotic report button 610, a physician antidepressant report button 611, a top 8 class quarterly report button 612, a physician allergy report button 613, a PMPM report button 614, a main menu button 615, and a PMPQ report button 616. The physician report menu 600 corresponds substantially to the physician report format 112 (FIG. 3), and facilitates the preparation of the desired physician reports. The main menu button 615 permits returning to the main menu screen 500 (FIG. 15).

A physician lipotropic utilization report 700 is shown in FIG. 17. The report 700 includes a title section 702 and a physician identification section 704. The drugs prescribed by the physician are set forth in the drug listing section 710, the number of prescriptions are set forth in the prescription section 712, the percentage of prescriptions are set forth in the section 713, and the cost of the particular prescription is set forth in the cost section 714.

The formats for the CCB report 602, physician 12 antagonist report 604, physician NSAID report 605, physician ACE inhibitor report 607, physician estrogen report 608, physician antibiotic report 610, physician antidepressant report 611, and physician allergy report 613 are substantially similar to the format of lipotropic report 700.

A top 8 class summary report or physician report card 800 is shown in FIG. 18. The report 800 includes a title section 802 and a physician identification section 804. The top 8 classes of drugs prescribed by a particular physician are set forth in a drug identification section 810 together with the particular drug prescribed. The number of prescriptions for each drug is set forth in the prescription section 812, and the corresponding cost for the prescription is identified in the cost section 814.

A top 8 quarterly utilization report 1000 is shown in FIG. 19. The report 1000 includes a title section 1002. The drug class, and particular drug name are set forth in the drug identification section 1010. Prescription information, including the number of prescriptions and the percentage of total prescriptions made, are set forth in quarterly increments as shown in first quarter increment, second quarter increment 1014, third quarter increment 1016 and fourth quarter increment 1018.

Figure 20:

A PMPM report 1100 is set forth in FIG. 20. The report 1100 includes a title section 1102. The physicians of the medical group 20 (FIG. 1) are identified in a physician identification section 1110. The members per month information for each of the physicians is identified for six different monthly periods, including monthly periods 1112, 1114, 1116, 1118, 1120 and 1122, but can be done for up to 12 monthly periods.

A physician top 25 drugs report 1130 is set forth in FIG. 21. The report 1130 includes a title section 1132, including the name of an individual physician. The top 25 drugs prescribed by the physician are identified in a drug section 1134. The number of prescriptions, and the cost of the prescriptions, are set forth in sections 1136 and 1138, respectively.

A PMPQ report 1140 is set forth in FIG. 22. The report 1140 includes a title section 1142 and a physician identification section 1144. The members per quarter information for each physician is identified in first quarter section 1145, second quarter section 1146, third quarter section 1147, and fourth quarter section 1148.

A physician brands vs. generics report 1150 is set forth in FIG. 23. The report 1150 includes a title section 1152, including the name of an individual physician. The total number of brand name drug prescriptions authorized by the physician are identified in section 1154, and the corresponding percentage of brand name drug prescriptions relative to the total number of prescriptions is identified in section 1155. The total number of generic drug prescriptions authorized by the physician are identified in section 1157, and the percentage of generic drug prescriptions relative to the total number of prescriptions is identified in section 1158.

To facilitate the searching and sorting of utilization information, a search screen 1200 (FIG. 24) is provided. The search screen 1200 includes a button row or tool bar 1202, and a search criteria section 1204.

Figure 25:
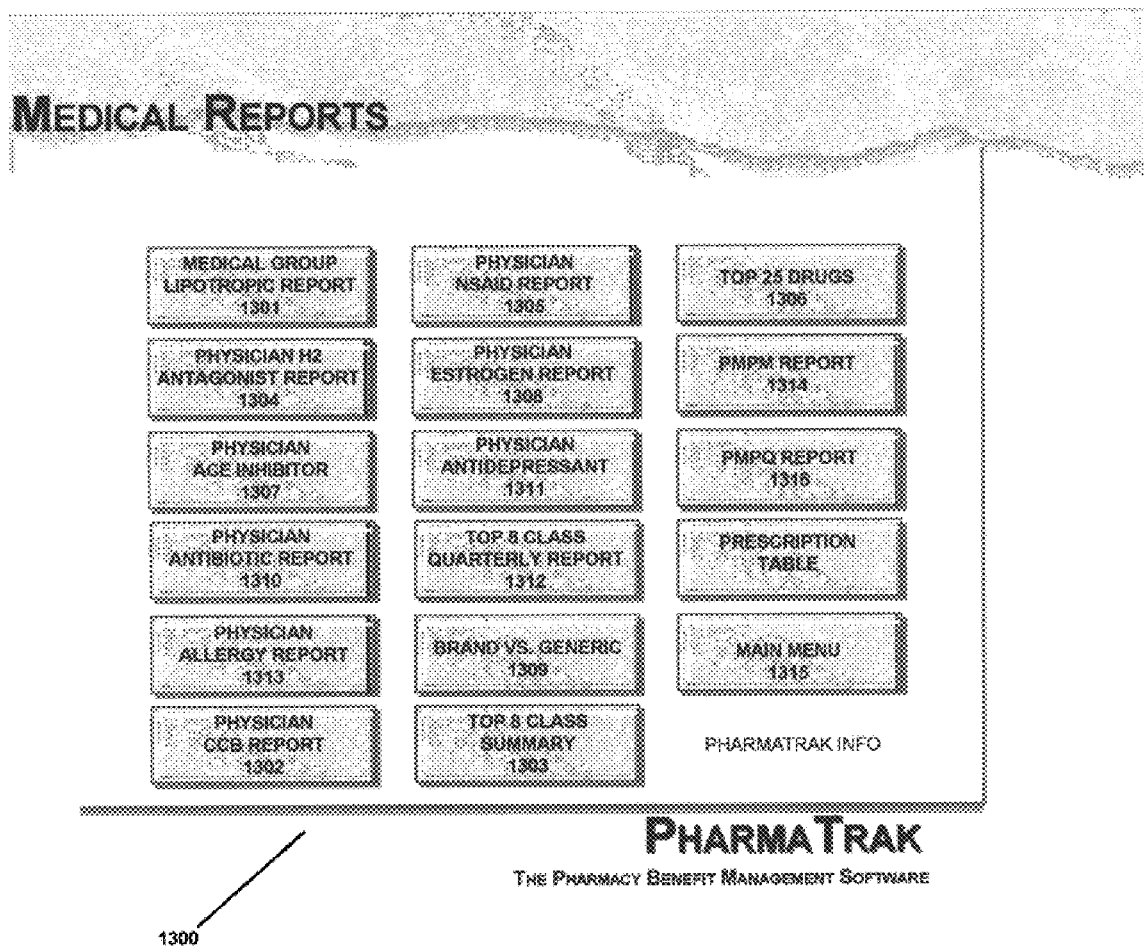

A medical group reports menu 1300 is shown in FIG. 25. The menu 1300 corresponds to the medical group report format selection 114 (FIG. 4). The menu 1300 includes a plurality of buttons for selecting report formats, including a medical group lipotropic report button 1301, a medical group CCB report button 1302, a top 8 therapeutic classes report button 1303, a medical group H2 antagonist report button 1304, a medical group NSAID report button 1305, a top 8 class quarterly report button 1306, a medical group ACE inhibitor button 1307, a medical group estrogen report button 1308, a main menu button 1309, a medical group antibiotic report button 1310, a medical group antidepressant report button 1311, a medical group allergy report button 1312, a PMPM report button 1313, a brand vs. generic report button 1314, a PMPQ report button 1315, and a top 25 drug report button 1316. The main menu button 1309 returns the display to the main menu screen 500 (FIG. 15).

A medical group search screen 1400 is shown in FIG. 26. The search screen 1400 includes a button row or tool bar 1402 and a selection criteria section 1404.

A medical group top 8 class summary report 15 is shown in FIG. 27. The report 1500 includes a title information section 1502. The drug class and names of drugs prescribed by physicians of the medical group are identified in drug section 1510. The associated member of prescriptions prescribed are set forth in the prescription section 1512, the corresponding percentage relative to the total number of prescriptions is set forth in section 1513, and the corresponding cost for the prescriptions are set forth in the cost section 1514.

A medical group lipotropic report 1600 is set forth in FIG. 28. The report 1600 includes a report title section 1602, and a drug identification section 1610 which identifies all the lipotropic drugs prescribed by the medical group 20 (FIG. 1). The number of prescriptions for each drug are set forth in the prescription section 1612, the corresponding percentage relative to the total number of prescriptions is set forth in section 1613, and the corresponding prescription cost is identified in the cost section 1614.

The formats for the medical group CCB report 1302, medical group H2 antagonist report 1304, medical group NSAID report 1305, medical group ACE inhibitor 1307, medical group estrogen report 1308, medical group antibiotic report 1310, medical group antidepressant report 1311, and medical group allergy report 1312 are substantially similar to the format of the medical group lipotropic report 1600.

A top 8 class quarterly utilization report 1700 is shown in FIG. 29. The utilization report 1700 includes a title section 1702. The drug class and name of drugs prescribed by the physicians of the medical group are set forth in the drug identification section 1710. The prescription information relating to each of the drugs in section 1710, including number of prescriptions and percent of total prescriptions, is set forth in quarterly increments, including first quarter increment 1712, second quarter increment 1714, third quarter increment 1716, and fourth quarter increment 1718.

Figure 30:

A medical group PMPM report 1800 is shown in FIG. 30. The report 1800 includes a title identification section 1802, and a listing of member physicians in physician identification section 1810. The member per month information for each physician is set forth in six monthly increments, including increments 1812, 1814, 1816, 1818, 1820 and 1822.

A PMPQ report 1830 is shown in FIG. 31. The report 1830 includes a title section 1832, and a listing of physicians in section 1834. The member per quarter information for each physician is set forth in quarterly increments, including first quarter increment 1835, second quarter increment 1836, third quarter increment 1837 and fourth quarter increment 1838.

A medical group brands vs. generics report 1840 is shown in FIG. 32. The report 1840 includes a title section, and a listing of member physicians in section 1844. The total number of brand name drug prescriptions authorized by each physician are identified in section 1845, and the corresponding percentage of brand name drug prescriptions relative to the total number of prescriptions is identified in section 1846. The total number of generic drug prescriptions authorized by the physicians are identified in section 1847, and the percentage of generic drug prescriptions relative to the total number of prescriptions is identified in section 1848.

A medical group top 25 drugs report 1850 is shown in FIG. 33. The report 1850 includes a title section 1852. The top 25 drugs prescribed by physician members of the medical group are identified in section 1854. The number of prescriptions for each drug, and the associated costs for the prescribed drugs, are identified in sections 1856 and 1858, respectively.

Figure 34:
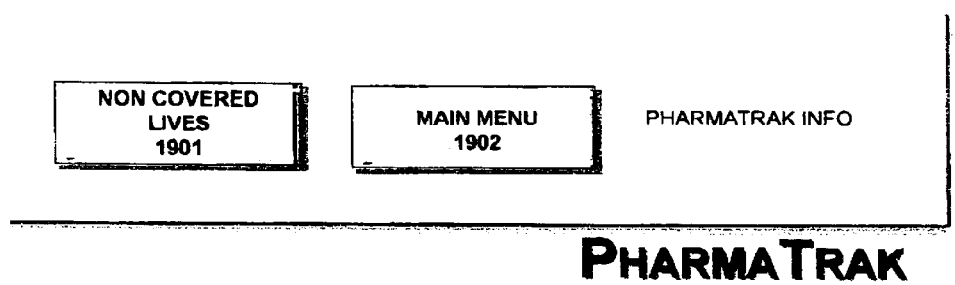

A miscellaneous reports screen 1900, corresponding to the miscellaneous reports format 116 (FIG. 5), is shown in FIG. 34. The screen 1900 a non covered lives report button 1901. The non covered lives button 1901 corresponds substantially to the non covered lives format selection 165 (FIG. 5). A main menu button 1902 returns the display to the main menu screen 500 (FIG. 15).

Figure 35:
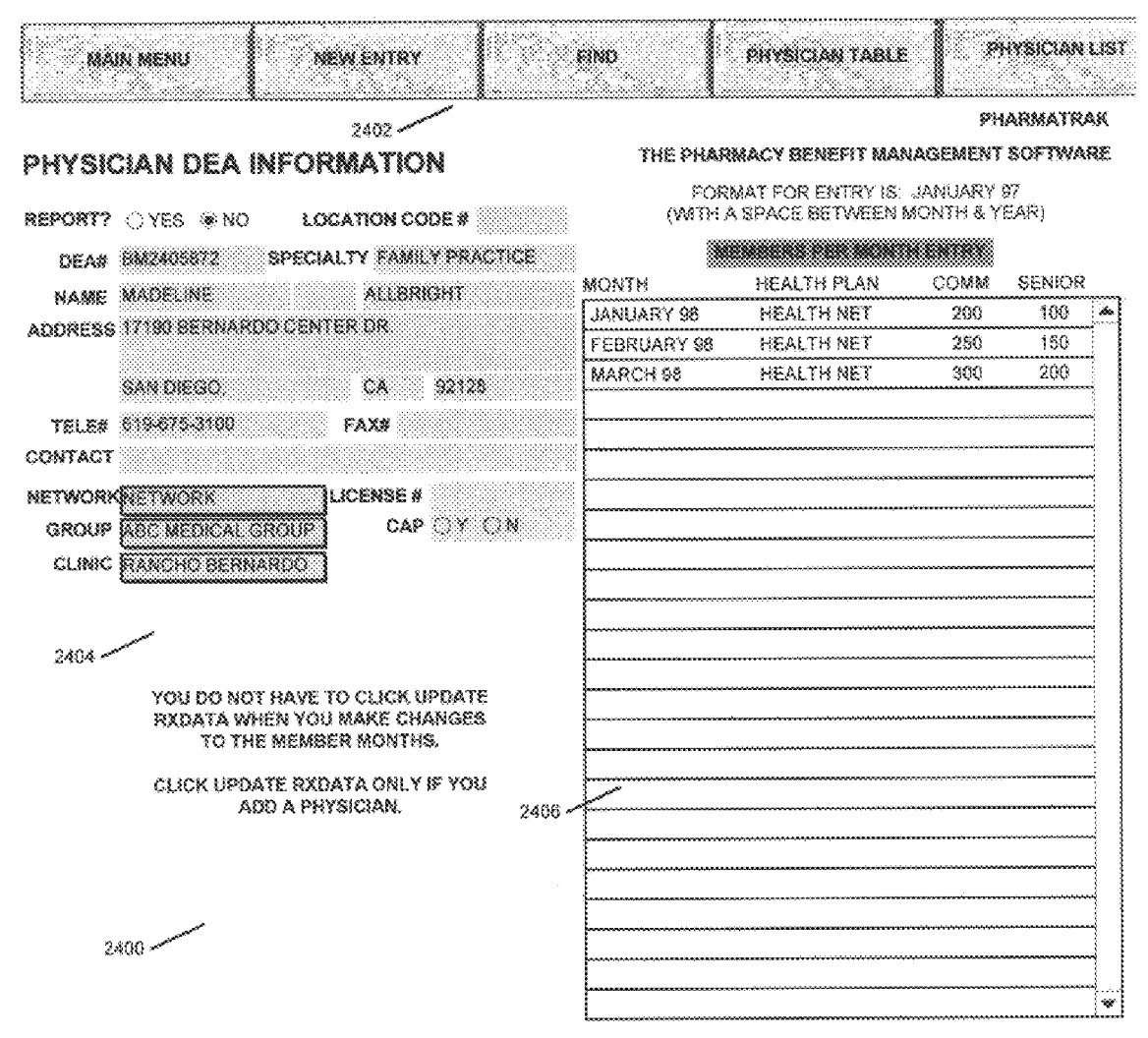

Physician information is entered via a physician information screen 2400 as shown in FIG. 35. The screen 2400 corresponds to the physician information selection 120 (FIGS. 2 and 7), and includes a button row or tool bar 2402. A physician DEA information section 2404 enables physician information to be entered for each physician. A members per month entry box 2406 permits members per month information to be entered for the physician on a month by month basis.

A physician list report 2500 is shown in FIG. 36, and corresponds to the physician list report selection 193 (FIG. 7). The report 2500 includes a title information section 2502. The report 2500 further includes a specialty section 2510 and a DEA name section 2512 to identify the physicians. A DEA address section 2514 and a telephone number/facsimile number section 2516 identifies the location where the physician operates a medical practice.

A therapeutic class number and name report 2600 is shown in FIG. 37. The report 2600 corresponds to the therapeutic class information selection 124 (FIGS. 2 and 9), and includes a button row or tool bar 2602 and a title information section 2604. The therapeutic class number and class name are set forth in the class number section 2610 and the class name section 2612. The drug name is identified in the drug name section 2614. The NDC code for the drugs are set forth in the NDC codes section 2616, and a linking name is identified for each drug in the drug name link section 2618.

Figure 38:
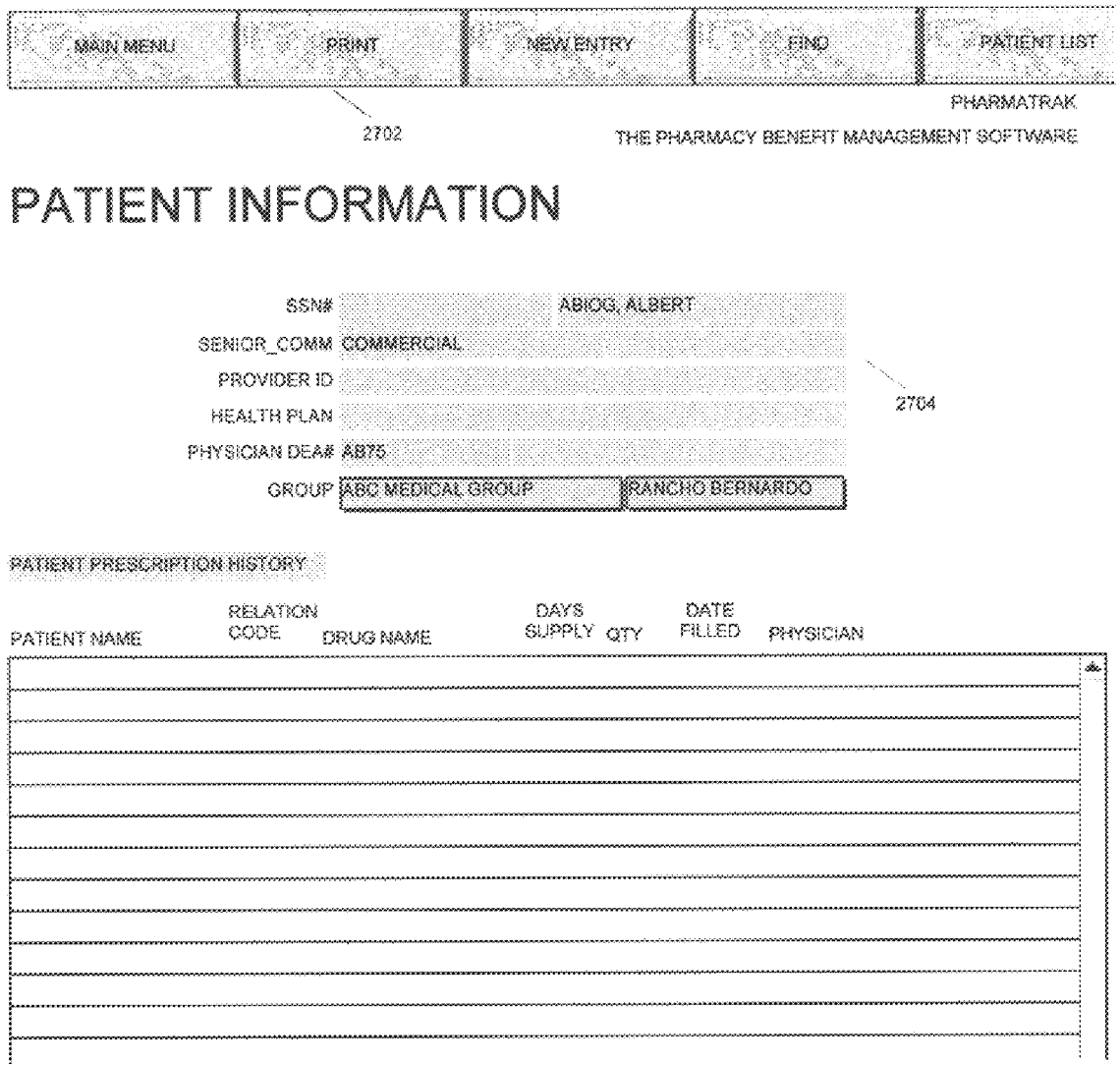

As described previously in connection with FIGS. 2 and 8, patient information can be entered according to the patient information selection 122. A patient information entry screen 2700 is shown in FIG. 38 to facilitate the entry of patient information. The screen 2700 includes a button row or tool bar 2702 and a patient information section 2704.

As described in connection with FIG. 8, a listing of patients can be provided. A patient list report 2800 is shown in FIG. 39. The report 2800 includes a title information section 2802. The patient names are set forth in a patient name section 2810, and the associated subscriber's social security number is set forth in social security number section 2812. The group identification number, and the provider identification number are indicated in group section 2814 and provider sections 2816 and 2818.

A prescription form screen 2900 is shown in FIG. 40. The screen 2900 displays data entry fields corresponding to data imported from the health care plan computers 50 and 60 (FIG. 1). As described in connection with FIG. 6, the medical group prescription information 52 and 62 is imported to the medical group computer 21 (FIG. 1) for use by the pharmacy benefit management software. The screen 2900 indicates the imported information, and includes a tool bar 2902. In addition, the screen 2900 includes a prescription information section 2910 which indicates the information received from the various health plan care computers 50 and 60.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A pharmacy benefit management system for monitoring the prescription activity of a medical group, the medical group contracting with a plurality of health plans, comprising:

pharmacy computer means for generating pharmacy claim information including prescribed drug information corresponding to the prescription activity;

a plurality of health plan computer means, each one associated with a different one of said plurality of health plans and each one being responsive to said pharmacy claim information for processing said prescribed drug information to generate medical group prescription information corresponding to the medical group;

medical group computer means configured for receiving and storing said medical group prescription information to facilitate an evaluation of the prescription activity;

means for transferring the medical group prescription information from all of said health plan computer means to the medical group computer means;

means for receiving at the medical group computer means medical group prescription information for the plurality of health plans;

means for determining the actual cost to the medical group for prescription drugs prescribed by doctors in the medical group, the means for determining being responsive to the prescription information for the plurality of health plans;

means for storing capitation benefits received from the plurality of health plans in said medical group computer means;

means for comparing the determined actual cost and said stored capitation benefits as received from the plurality of health plans; and report means for processing said stored medical group prescription information to generate utilization information indicative of the prescription activity for enabling the medical group to monitor the prescription activity to determine if the prescription activity should be modified.

2. A system according to claim 1, further including pharmacy benefit computer means for accumulating said pharmacy claim information and for transmitting said accumulated pharmacy claim information to said health plan computer means.

3. A system according to claim 1, wherein said pharmacy computer means includes a plurality of pharmacy computers corresponding to a plurality of pharmacies, each one of said pharmacy computers generating pharmacy claim information including prescribed drug information corresponding to prescriptions received at respective ones of said pharmacies.

4. A system according to claim 1, wherein said health plan computer means includes a plurality of health plan computers corresponding to the plurality of health care plan organizations, each one of said health plan computers processes said prescribed drug information corresponding to a respective one of said health care plan organizations to generate said medical group prescription information corresponding to the medical group and associated with said respective one of said health care plan organizations.

5. A system according to claim 1, wherein said medical group computer means further stores physician information for physicians associated with the medical group.

6. A system according to claim 5, wherein said report means includes physician report means for generating physician reports.

7. A system according to claim 6, wherein said physician reports indicate particular drugs prescribed by said physicians.

8. A system according to claim 5, wherein said report means includes medical group report means for generating medical group reports.

9. A system according to claim 8, wherein said medical group reports indicate particular drugs prescribed by said physicians.

10. A method of monitoring the prescription activity of a medical group, the medical group having contracts with one or more health plans that provide prescription drug capitation, comprising:

collecting pharmacy claim information from a plurality of pharmacies, the pharmacy claim information including prescribed drug information, prescribing doctor information, and health plan identification, corresponding to the prescription activity;

processing said pharmacy claim information to generate medical group prescription information corresponding to the medical group, the medical prescription information selected for the contracted health plans;

transferring the medical group prescription information to a medical group computer means;

determining from the medical group prescription information actual costs to the medical group for prescription drugs prescribed by doctors associated with the medical group, an actual cost being determined separately for each of the contracted health plans;

comparing the determined actual costs of prescription drugs to capitation benefits received from the contracted health care plans;

evaluating the adequacy of the capitation received from the contracted health care plans;

receiving and storing said medical group prescription information to facilitate an evaluation of the prescription activity;

processing said stored medical group prescription information to generate utilization information indicative of the prescription activity for enabling the medical group to monitor the prescription activity to determine if the prescription activity should be modified; and health plan computers corresponding to a plurality of health care plan organizations, and generating said medical group prescription information at each one of said health plan computes corresponding to the medical group and associated with said respective one of said health care plan organizations.

11. A method according to claim 10, further including accumulating said pharmacy claim information and transmitting said accumulated pharmacy claim information.

12. A method according to claim 10, further including using a plurality of pharmacy computers corresponding to the plurality of pharmacies, and generating pharmacy claim information including prescribed drug information corresponding to prescriptions received at respective ones of said pharmacies.

13. A method according to claim 10, further including storing physician information for physicians associated with the medical group.

14. A method according to claim 13, further including generating physician reports.

15. A method according to claim 14, further including indicating particular drugs prescribed by said physicians.

16. A method according to claim 13, further including generating medical group reports.

17. A method according to claim 16, further including indicating particular drugs prescribed by said physicians.

* * * * *